(12) United States Patent
Lee et al.

(10) Patent No.: US 9,056,886 B2
(45) Date of Patent: Jun. 16, 2015

(54) GUANOSINE-RICH MODIFIED OLIGONUCLEOTIDES AND ANTIPROLIFERATIVE ACTIVITY THEREOF

(75) Inventors: Soo Jin Lee, Suwon-si (KR); Sung Hwan Moon, Suwon-si (KR)

(73) Assignee: APTABIO THERAPEUTICS INC., Suwon-Si, Gyeonggi-Do (KR)

( * ) Notice: Subject to any disclaimer, the term of this patent is extended or adjusted under 35 U.S.C. 154(b) by 172 days.

(21) Appl. No.: 13/381,326

(22) PCT Filed: Jun. 29, 2010

(86) PCT No.: PCT/KR2010/004202
§ 371 (c)(1),
(2), (4) Date: Dec. 28, 2011

(87) PCT Pub. No.: WO2011/002200
PCT Pub. Date: Jan. 6, 2011

(65) Prior Publication Data
US 2012/0202981 A1      Aug. 9, 2012

(30) Foreign Application Priority Data

Jun. 29, 2009   (KR) .................. 10-2009-0058498
May 31, 2010   (KR) .................. 10-2010-0051202

(51) Int. Cl.
*C07H 19/173*         (2006.01)
*C07H 21/00*          (2006.01)

(52) U.S. Cl.
CPC .............. *C07H 19/173* (2013.01); *C07H 21/00* (2013.01)

(58) Field of Classification Search
USPC ................ 435/6, 91.1, 91.31, 455, 6.1, 6.11; 514/1, 2, 44; 536/23.1, 24.5
See application file for complete search history.

(56) References Cited

U.S. PATENT DOCUMENTS

| 5,457,187 | A | 10/1995 | Gmeiner et al. |
| 5,567,604 | A | 10/1996 | Rando et al. |
| 5,614,505 | A | 3/1997 | Gmeiner et al. |
| 6,994,959 | B1 | 2/2006 | Tam |
| 7,312,082 | B2 | 12/2007 | Neidle et al. |
| 7,314,926 | B1 * | 1/2008 | Miller et al. .................. 536/24.1 |
| 7,357,928 | B2 * | 4/2008 | Bates et al. .................. 424/130.1 |
| 2004/0018483 | A1 | 1/2004 | Neidle et al. |
| 2005/0159375 | A1 | 7/2005 | Srivastava et al. |
| 2007/0105805 | A1 | 5/2007 | Kmiec et al. |
| 2009/0226914 | A1 * | 9/2009 | Bates et al. .................. 435/6 |
| 2011/0105422 | A1 * | 5/2011 | Acton et al. .................. 514/34 |
| 2012/0149888 | A1 * | 6/2012 | Srivastava et al. .......... 536/23.1 |

FOREIGN PATENT DOCUMENTS

| JP | 10218893 A | 8/1998 |
| JP | 2002541264 A | 12/2002 |
| JP | 2003526682 A | 9/2003 |
| JP | 2007531699 A | 11/2007 |
| JP | 2010504750 A | 2/2010 |
| WO | 94/08053 | 4/1994 |
| WO | 9419362 A1 | 9/1994 |
| WO | 9532628 A1 | 12/1995 |
| WO | 03/002592 | 1/2003 |
| WO | 03002592 A1 | 1/2003 |
| WO | 03/087317 | 10/2003 |

OTHER PUBLICATIONS

International Preliminary Report on Patentability for PCT/KR2010-004202 dated Jan. 4, 2012.
International Search Report mailed Jun. 16, 2011 for PCT/KR2010/004202.
Yan Xu et al., "Highly Efficient Photochemical 2'-Deoxyribonolactone Formation at the Diagonal Loop of a 5-Iodouracil-Containing Antiparallel G-Quartet", J. Am. Chem. Soc., 2004, pp. 6274-6279, vol. 126, No. 20.
Japanese Office Action for application No. 2012-518491 dated Sep. 16, 2014.
T.D. Sakore et al., "Mutagen-nucleic acid intercalative binding: Structure of a 9-amino-acridine: 5-iodocytidylyl(3'-5') guanosine crystalline complex", Proc. Natl. Acad. Sci. USA, Jan. 1977, pp. 188-192, vol. 74, No. 1.
Benjamin N. Conner et al., "Helix Geometry and Hydration in an A-DNA Tetramer: IC-C-G-G", Journal of Molecular Biology, Apr. 25, 1984, pp. 663-695, vol. 174, No. 4, Academic Press Inc. (London) Ltd.
David A. Zarling et al., "Immunoglobulin Recognition of Synthetic and Natural Left-handed Z DNA Conformations and Sequences", Journal of Molecular Biology, Jul. 5, 1984, pp. 369-415, Vo. 176, No. 3, Academic Press Inc. (London) Ltd.
David G. Osterman et al., "5-Fluorocytosine in DNA Is a Mechanism-Based Inhibitor of Hha I Methylaset", Biochemistry, 1988, pp. 5204-5210, vol. 27, No. 14, American Chemical Society.
Ulf Pindur et al., "Antitumor Active Drugs as Intercalators of Deoxyribonucleic Acid", Journal of Chemical Education, Apr. 1, 1993, pp. 263-272, vol. 70, No. 4.
Matthew A. Young et al., "Analysis of Local Helix Bending in Crystal Structures of DNA Oligonucleotides and DNA-Protein Complexes", Biophysical Journal, Jun. 1, 1995, pp. 2454-2468, vol. 68, No. 6, the Biophysical Society.
Jiro Kondo et al., "Crystal structures of a DNA octaplex with I-motif of G-quartets and its splitting into two quadruplexes suggest a folding mechanism of eight tandem repeats", Nucleic Acids Research, May 7, 2004, pp. 2541-2549, vol. 32, No. 8, Oxford University Press.
Julian Bertschinger et al., "Covalent DNA display as a novel tool for directed evolution of proteins in vitro", Protein Engineering, Design & Selection, Nov. 2, 2004, pp. 699-707, vol. 17, No. 9, Oxford University Press.
Benjamin N. Conner et al., "The molecular structure of d(ICpCpGpG), a fragment of right-handed double helical A-DNA", Nature, Jan. 28, 1982, pp. 294-299, vol. 295, Macmillan Journals Ltd.
European Office Action dated Apr. 4, 2014.

* cited by examiner

*Primary Examiner* — Jane Zara
(74) *Attorney, Agent, or Firm* — Lowe Hauptman & Ham, LLP

(57) ABSTRACT

The present invention relates to a novel modified oligonucleotide comprising at least one guanosine molecule and a modified nucleic acid with therapeutic efficacies. The present invention also relates to a pharmaceutical composition having cell apoptotic activity against cancer cells for preventing or treating cancer comprising a guanosine-rich modified oligonucleotide with at least one therapeutically effective modified nucleic acid (N), or its pharmaceutically acceptable salt as active ingredient.

2 Claims, 6 Drawing Sheets

GUANOSINE-RICH MODIFIED OLIGONUCLEOTIDES AND ANTIPROLIFERATIVE ACTIVITY THEREOF

CROSS REFERENCE TO RELATED APPLICATION

This application claims the priority of Korean Patent Application No. 10-2009-0058498, filed on Jun. 29, 2009 in the KIPO (Korean Intellectual Property Office), and Korean Patent Application No. 10-2010-0051202, filed on May 31, 2010 in the KIPO (Korean Intellectual Property Office). Further, this application is the National Phase application of International Application No. PCT/KR2010/004202, filed on Jun. 29, 2010, which designates the United States and was published in English.

SEQUENCE LISTING

The instant application contains a Sequence Listing which has been submitted in ASCII format via EFS-Web and is hereby incorporated by reference in its entirety. Said ASCII copy, created on Apr. 20, 2012, is named 51090028.txt and is 38,344 bytes in size.

TECHNICAL FIELD

The present invention relates to a modified oligonucleotide comprising at least one guanosine molecule and modified nucleic acid, with therapeutic efficacies. The present invention also relates to a pharmaceutical composition for preventing or treating cancer comprising the modified nucleic acid or its pharmaceutically acceptable salt as an active ingredient.

BACKGROUND ART

Even with the recent rapid progress in medical technology and treatment cancer is still regarded as one of the most lethal diseases in the world. Further, the global trend of aging society simply speeds up the annual increase in the number of cancer patients. In general, anticancer agents are extremely toxic and they cannot selectively remove cancer cells. Therefore, there has been a long-felt need for the development of an anticancer agent which is very effective but with less toxicity.

Since the development of an automated DNA synthesis in 1980s, research in medical field has been conducted more actively to develop therapeutic agents using siRNA and antisenses which target intracellular mRNAs, aptamers, CpG and decoy which target ribozymes and proteins, etc. [Gleave et al., Nat Rev Cancer. 2005 468-479; Castanotto et al., Nature 2008 426-433; Sullenger et al., Nature 2002 252-258; Kaur et al., Expert Opin Investig Drugs. 2008 43-60; Jurk M et al., BioDrugs. 2007 387-401; Tomita et al., Clin Exp Nephrol. 2007 7-17].

Guanosine-rich oligonucleotides have been known to have an inhibitory activity against growth of broad spectrum of cancer cells. When cancer cells are treated with guanosine-rich oligonucleotides, they bind to particular proteins in the cells, for example, eEF1A, JNK, Ki-ras, Nucleolin, stat3, telomerase, topoisomerase, which are closely associated with cell growth and death, and regulate the cell cycle. These proteins are known to be overexpressed in cancer cells than in normal cells [Christopher R. Ireson et al., Molecular cancer therapy 2006 2957-2962; Naijie Jing et al., Cancer Research 2004 6603-6609; Christophe Marchand et al., The journal of Biological Chemistry 2002 8906-8911].

These guanosine-rich oligonucleotides have a special structure including a triple hydrogen bond with cytosine. They can have a structure with a quadruple strand via an intramolecular or intermolecular binding. Instead of forming a double helix structure by a hydrogen bond between adenosine-thymidine and guanosine-cytidine, four guanosine molecules are located on a single plane to form a hydrogen bond in Hoogsten type thereby forming G-quadruplex. This G-quadruplex is repeated at least once and form a tetrad helical structure.

In general, oligonucleotides have not been favored in developing new drugs due to the low blood stability and cell permeability. However, oligonucleotides with G-quadruplex structure are known to have stably structure and relatively high blood stability and cell permeability [Julian Leon Huppert, Chemical Society Reviews 2008, 37, 1375-1384; Paula J. Bates et al., Experimental and Molecular Pathology (2009) 151-164; Christopher R. Ireson et al., Molecular cancer therapy 2006 2957-2962]. U.S. Pat. No. 7,312,082 teaches that the stability of G-quadruplex depends on the monovalent cations, interchelating agents, and concentration of oligonucleotides or the like. (Haiyan Qi et al., Cancer Res 2006 11808-11816, Anna Arola et al., Current Topics in Medicinal Chemistry 2008 1405-1415).

U.S. Pat. No. 7,314,926 and U.S. Pat. Appl. Publ. No. 2007-105805 disclose that G-Quadruplexes bind to certain proteins, which are expressed on the surface of cancer cells, enter cancer cells by endocytosis, and bind to proteins involved in cell apoptosis thereby inhibiting growth of cancer cells. The cell apoptosis is known to be induced by cytostatic effect rather than cytotoxic effect [Paula J. Bates et al. The journal of Biological Chemistry 1999 26369-26377; Bruna et al., FEBS 2006 1350-1361].

In addition to their inhibitory effect against cancer cell growth, other effects of G-Quadruplex forming oligonucleotides, have been also known. For example, U.S. Pat. No. 5,567,604 discloses antiviral effect; U.S. Pat. No. 6,994,959 discloses effect in immune regulation; and U.S. Pat. Appl. Publ. No. 2007-105805 discloses its role in the treatment of Huntington's disease thus suggesting that they are associated with various biological functions and regulations in the body [Cheryl A. Stoddart et al. Antimicrobial Agents and Chemotherapy 1998 2113-2115; Michael Skogen et al. BMC Neuroscience, 2006 7:65]. Many lines of research have been focused on using G-quadruplex forming oligonucleotides the treatment of various diseases and recently a clinical study has been carried out to prove its potential as an anticancer agent [Paula J. Bates et al. Experimental and Molecular Pathology (2009) 151-164].

AS-1411, a clinical drug developed as a result, is a G-Quadruplex forming oligonucleotide, which binds to nucleolin which are overly expressed in cancer cells thereby exert excellent inhibitory activity against cancer cell growth. Besides, it can considerably reduce its influence on normal cells in the body while increasing its cell apoptotic activity against cancer cells are thus expected to be a new potential anticancer drug [Christopher R. Ireson et al., Mol Cancer Ther. 2006 December; 5(12): 2957-62]. G-quadruplex forming oligonucleotides induce cell apoptosis by inhibiting cell growth. However, there are disadvantages with the G-quadruplex forming oligonucleotides that it is essential to provide a patient with a daily ringer injection for a period of 4-7 days due to their relatively low cytotoxicity, and also there is a burden for the need of combinatorial administration of a chemotherapeutic agent which is highly toxic [Paula J. Bates Et, al. Experimental and Molecular Pathology (2009) 151-164; Christopher R. Ireson et al., Molecular cancer therapy 2006 2957-2962].

To solve the above problems, the inventors of the present invention have made efforts to improve the cell apoptotic effect of the G-quadruplex forming oligonucleotides by introducing therapeutically effective modified nucleic acid having apoptotic effect to the G-quadruplex forming oligonucleotides.

A representative example of therapeutically effective modified nucleic acids is 5-fluorouracil (5-FU). 5-FU was first developed in late 1950.s as an anti-metabolic anticancer agent. It is known to exert anticancer activity by blocking thymidylate synthase [Piedo et al., J Clin Oncol 1988, 1953-1664]. In addition, prodrugs in the form of a 5-fluoropyrimidine nucleoside such as 5-fluorodeoxyuridine(5-FdU), 5-fluorodeoxycytidine(5-FdC), 5-fluorouridine have been used for, the treatment of colorectal cancer, breast cancer, and head and neck cancer for more than 4 decades and they are under clinical experiment [Thomas et al., Clin Exp Pharmacol Physiol. 1998 887-895; Heidelberger et al. Nature 1957 179:663-666; Longley et al., Nat Rev Cancer 2003 330-338; Beumer et al., Cancer Chemother Pharmacol 2008 363-368; Song et al., Clinical cancer research. 1997, 901-909]. Since the synthesis of phosphoramidite preparations, comprising these 5-fluorodeoxyuridine, 5-fluorodeoxycytidine, 5-fluorouridine nucleoside in the oligonucleotides, was enabled, it was made possible to synthesize in a solid phase DNA synthesizer the oligonucleotides containing therapeutic nucleosides [Gmeiner et al., J. Org. Chem. 1994, 5779-5783; Schmidt et al., Nucleic Acids Research, 1992, 2421-2426; Stolarski et al., Biochemistry 1992, 31, 7027-7042].

These therapeutic nucleosides-containing oligonucleotides release 5-FdU and 5-FdC during the enzymatic degaration by exonucleases, and become associated with various kinds of enzymes to be converted into 5-FdUMP as a fully activated form thereby inducing cell apoptosis. Thus obtained oligonucleotides are known to be more cytotoxic than 5-FdU at equal concentration, and are also therapeutically more effective in treating drug-resistant cancer cells [Gmeiner et al., Nucl. Nuct. 1995 243-253].

U.S. Pat. No. 5,457,187 discloses the cytotoxicity of homo poly-FdU oligonucleotide containing 5-fluoro uracil, and U.S. Pat. No. 5,614,505 discloses the cytotoxicity of oligonucleotides comprising FdU. However, these 5-fluoro uracil-containing oligonucleotides do not form G-quadruplex and have a very low blood stability and cell permeability, thus not being suitable to be developed as a drug with respect to their structure and pharmaceutical efficacies.

DISCLOSURE OF INVENTION

Subjects to be Solved

The inventors of the present invention, in an effort to solve the above-described problems associated with prior art, discovered that, by introducing at least one therapeutically effective modified nucleic acid, which is capable of inducing cell apoptosis due to cytotoxic effect, into oligonucleotides, which form a G-quadruplex due to the presence of abundant guanosines with cytotoxic effect, blood stability and cell permeability of the oligonucleotide were considerably improved while the growth of cancer cells was more effectively inhibited being ultimately led to apoptosis. Upon comparison of the cytotoxic effect of the above-mentioned oligonucleotides synthesized thereof, it was confirmed that their cytotoxic effect against cancer cells was superior to those of a clinical drug.

Therefore, the present invention relates to a novel guanosine-rich modified oligonucleotide containing a therapeutically effective modified nucleic acid.

Further, the present invention also relates to a pharmaceutical composition for preventing and treating cancer comprising the above-mentioned modified oligonucleotide or its pharmaceutically acceptable salt as active ingredient.

Technical Solution

The present invention relates to a modified oligonucleotide having a structure of G-quadruplex comprising a compound represented by the following formula 1 or 2.

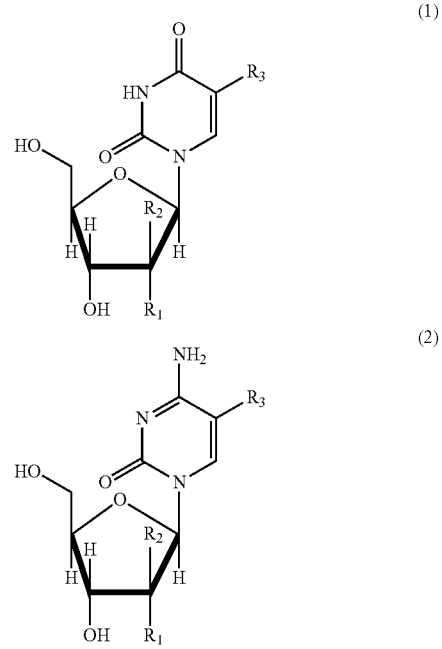

In the above formula 1 or 2, $R_1$ is a hydrogen, a halogen or a hydroxyl group, $R_2$ is a hydrogen, a halogen or a hydroxyl group, $R_3$ is a hydrogen, a halogen, $C_{1-10}$ alkyl, $C_{1-10}$ haloalkyl, $C_{2-10}$ alkenyl, $C_{2-10}$ haloalkenyl, wherein $R_1$, $R_2$ are not a hydroxyl group at the same time.

Further, the present invention also relates to an oligonucleotide sequence called 'GxHyNz', wherein G is guanosine or its derivative; H is a nucleic acid exclusive of guanosine; N is uridine or cytidine-derived modified nucleic acid with therapeutic efficacies, wherein G, H, N are randomly arranged; x is an integer of 1-30, y is an integer of 0-30, z is an integer of 1-30, wherein the sum of (x+y+z) is not greater than 60;

Further, the present invention also relates to a pharmaceutical composition for preventing and treating cancer comprising the above-mentioned modified oligonucleotide or its pharmaceutically acceptable salt as an active ingredient.

Effect of the Invention

The modified oligonucleotide of the present invention is a compound with a novel chemical structure comprising at least one therapeutically effective modified nucleic acid and guanosine capable of forming a G-quadruplex structure. It has an excellent cell apoptotic activity and is thus suitable as a therapeutic agent for preventing and treating cancer.

BRIEF DESCRIPTION OF DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

BEST MODE FOR CARRYING OUT THE INVENTION

The present invention is described in further detail as set forth hereunder.

The present invention relates to an oligonucleotide prepared in such a fashion that a guanosine-rich nucleotide, which enables to form a G-quadruplex structure, is introduced with a modified nucleic acid to be endowed with cytotoxicity.

Figure 1:
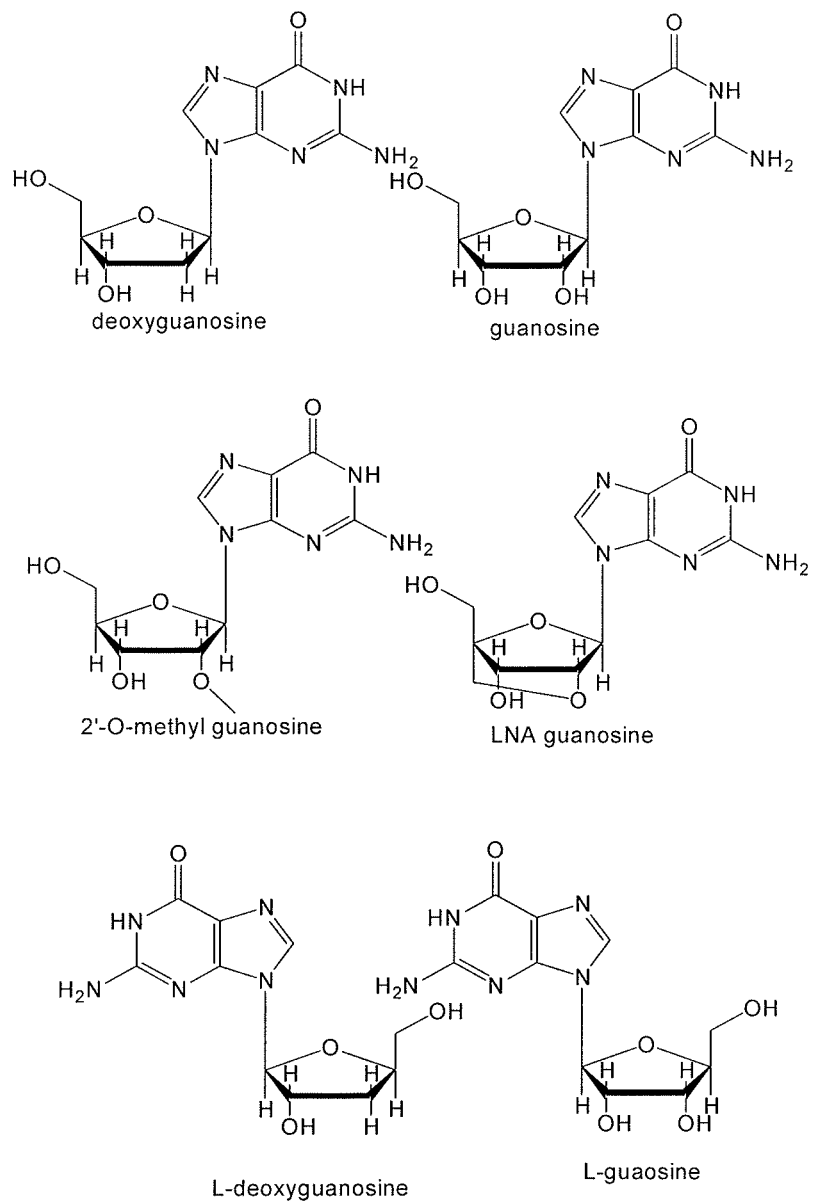
FIG. 1 shows a guanosine or its derivatives.

The G-quadruplex used in the present invention is rich in at least one representative guanosine (G) selected from the group consisting of 2-deoxy-guanosine, guanosine, 2'-O-methyl-guanosine, 2'-F-guanosine, LNA (Locked Nucleic Acid)-guanosine, D-deoxyguanosine and D-guanosine (FIG. 1). In a G-quadruplex oligonucleotide, four guanosine molecules are located on a single plane to form a hydrogen bond in Hoogsten type thereby forming a tetrad helical structure, and a modified nucleic acid with therapeutic efficacy is introduced to this oligonucleotide in the present invention.

The guanosine-rich oligonucleotide that forms a G-quadruplex structure has been known to selectively bind to cancer cells and also inhibit the growth of cancer cells in cells via various mechanisms. When the G-quadruplex structure-forming oligonucleotide is introduced with at least one modified nucleic acid and then transported inside cancer cells, the cell growth inhibiting effect by G-quadruplex structure itself and the direct cell growth inhibiting effect by the modified nucleic acid, which is given a therapeutic effect when degraded by a nuclease, work together to eventually lead the cancer cells into death. The G-quadruplex structure-forming oligonucleotide alone can only exert the cell growth inhibiting effect and it does not have high cell apoptotic effect thus requiring a long and continued treatment for a certain period of time. However, the addition of therapeutically effective modified nucleic acid into the G-quadruplex structure-forming oligonucleotide of the present invention confirmed that it considerably improved cell apoptotic effect thereby considerably increasing cell apoptosis rate.

Examples of therapeutically effective nucleic acids are adenosine, guanosine, thymidine, cytidine, and uridine wherein their sugar or base is modified. More specifically, the modified nucleic acids derived from uridine or cytidine used in the present invention are preferably pyrimidine type nucleosides such as uridine of the following formula 1 or cytidine of the following formula 2. These nucleosides can be converted into phosphoramidite by using a conventional method [Oligonucleotides and Analogues: A Practical Approach 1991 Fritz Eckstein et al. IRL Press: Oxford]; or nucleotide phosphoramidite may be purchased from companies (e.g., Glenresearch, Berry and Associates, Okeanos Tech, Chemgene, Proligo), and then introduced to a guanosine-rich oligonucleotide via solid phase synthesis using a DNA synthesizer according to a known method.

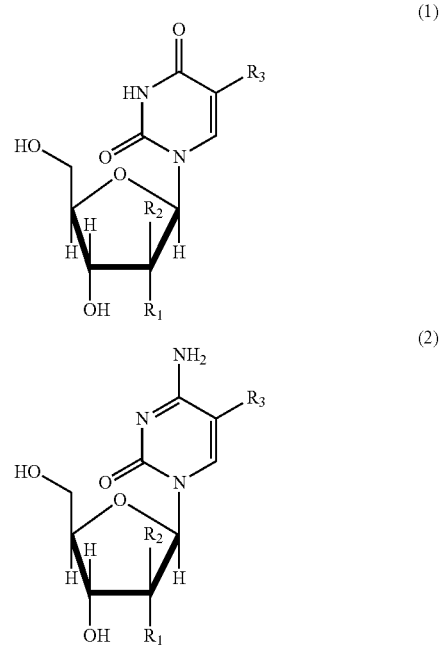

In the above formula 1 or 2, R1 is a hydrogen, a halogen or a hydroxyl group, $R_2$ is a hydrogen, a halogen or a hydroxyl group, $R_3$ is a hydrogen, a halogen, $C_{1-10}$ alkyl, $C_{1-10}$ haloalkyl, $C_{2-10}$ alkenyl, $C_{2-10}$ haloalkenyl, wherein $R_1$, $R_2$ are not a hydroxyl group at the same time.

The above uridine- or cytidine-derived modified nucleic acids (N) are preferably 5-fluorodeoxyuridine, 5-fluorouridine, 5-fluorodeoxycytidine, 5-fluorocytidine, 5-iododeoxyuridine, 5-iodouridine, 5-iododeoxycytidine, 5-iodocytidine, cytosine arabinoside/Ara-C, 2',2'-difluorodeoxycytidine/gemcitabine, capecitabine and bromovinyl-deoxyuridine. The above modified nucleic acids are first converted in the form of phosphoramidite and then prepared into a modified oligonucleotide via solid phase synthesis using a DNA synthesizer according to a known method. That is, the modified oligonucleotide is synthesized by dissolving the above modified nucleic acid phosphoramidite in anhydrous acetonitrile and loading it onto a DNA synthesizer according to the protocol provided by Glenresearch Corporation or the conventional synthesis and purification methods disclosed in U.S. Pat. Nos. 5,457,187 and 5,614,505. One example of thus synthesized modified oligonucleotides is shown below in formula 3.

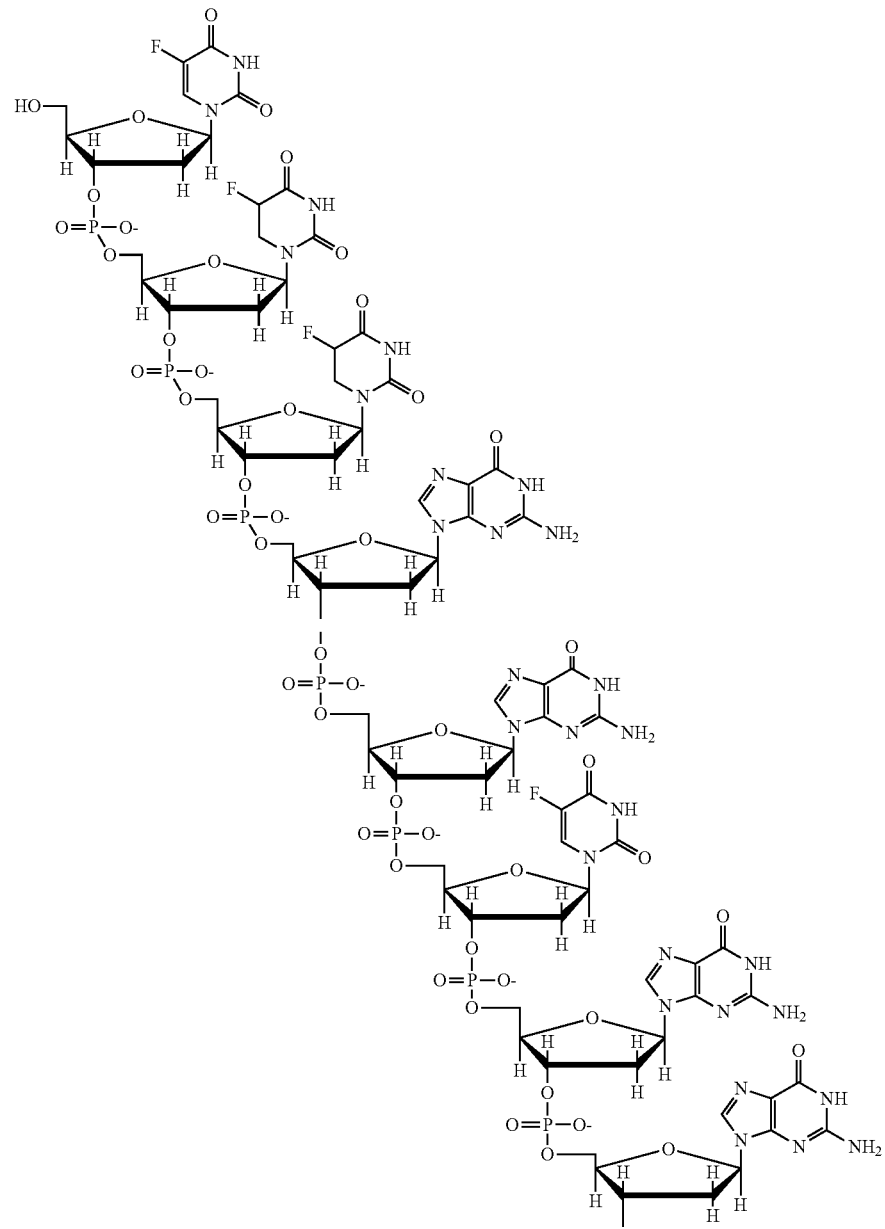
(3)

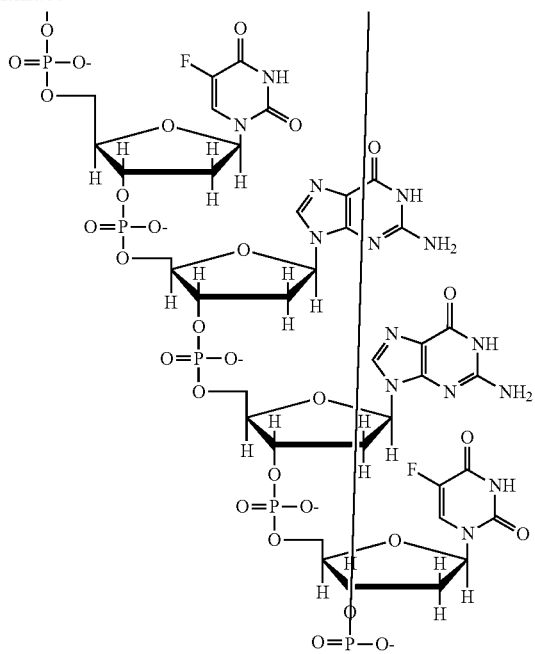
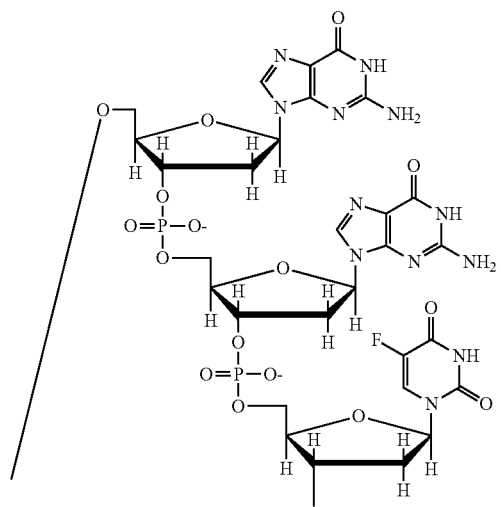

-continued
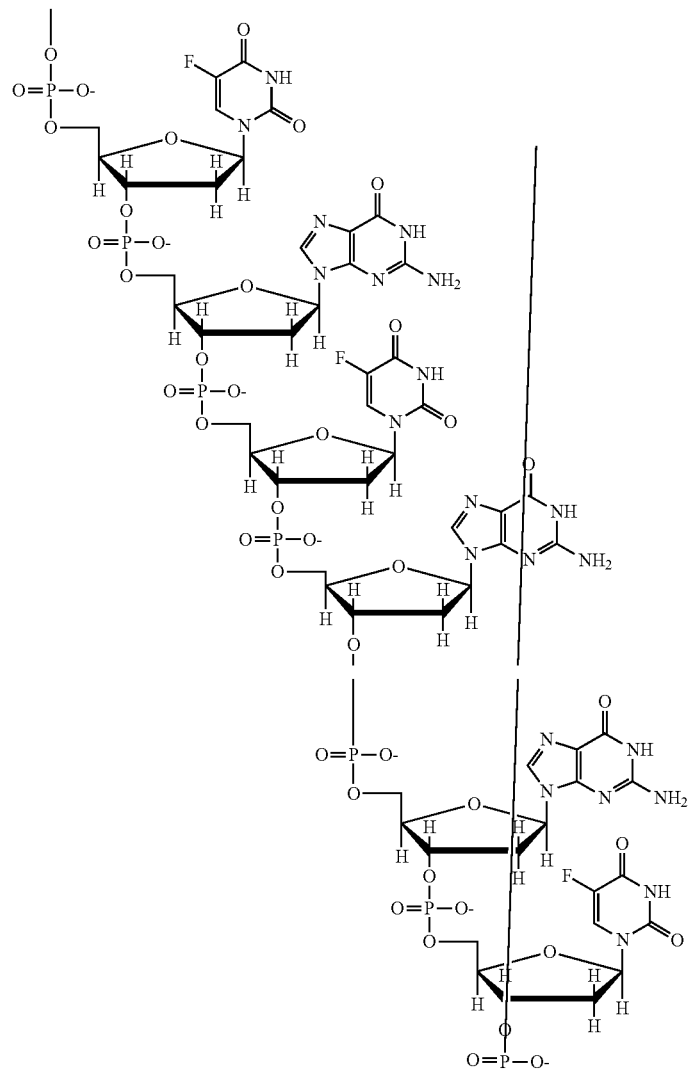
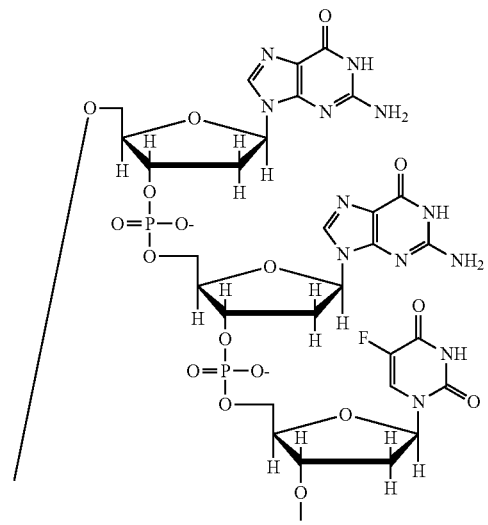

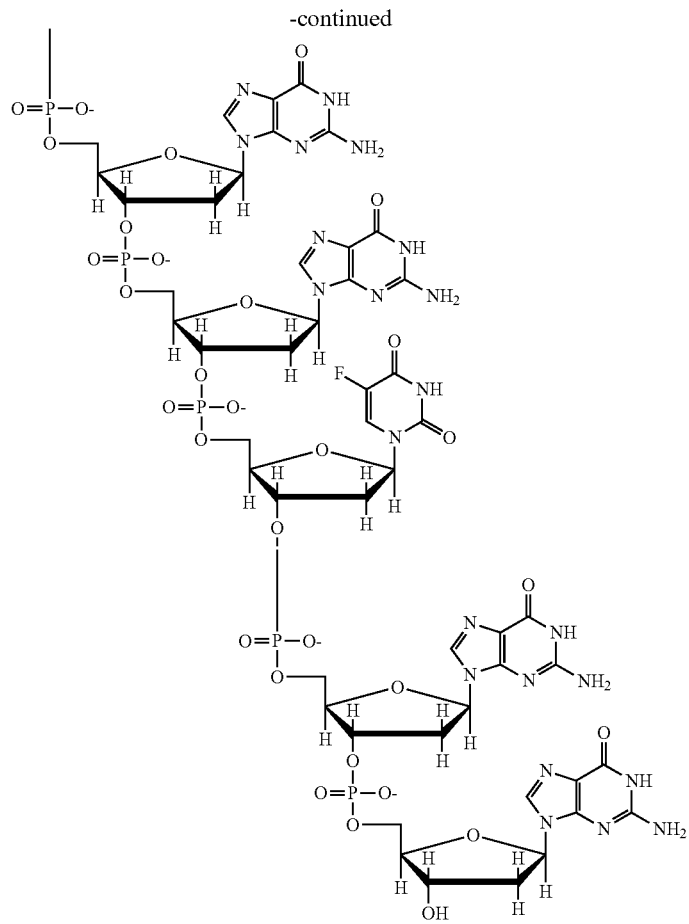

Further, the representative examples of the sequences of modified oligonucleotides that can be synthesized by using the modified nucleic acids, with regard to the oligonucleotide sequences already reported for the purpose of therapeutic treatment [Paula J. Bates et al., The journal of Biological Chemistry 1999 26369-26377, Cheryl A Stoddart et al., Antimicrobial agents and chemotherapy 1998 2113-2115, Virna Dapic et al. Biochemistry 2002 3676-3685, Naijie Jing et al., Biochemistry 2002, 41, 5397-5403, Naijie Jing et al., Cancer research 2004 6603-6609, Haiyan Qi et al., Cancer research 2006 11808-11816, YunTeng et al. Cancer Research 200710491-10500, Bruna Scaqqiante et al., FEBS Journal 2006 1350-1361, Julie E. Reed et al., Journal of the American Chemical Society 2006 5992-5993, Jeffrey S. Bishop et al., The Journal of Biological Chemistry 1999 5698-5703, Christophe Marchand et al., The Journal of Biological Chemistry 2002 8906-8911, Jun-ichiro Suzuki et al., Journal of virology 2002 3015-3022, Virna Dapic et al., Nucleic Acids Research, 2003 2097-2107, Amber Goodchild et al. Nucleic acid research 2007 4562-4572, U.S. Pat. Nos. 6,323,185, 7,314, 926, 6,994,959, 7,157,436, and 71992281, or to the various oliqonucleotide sequences with G-quadruplex structure exhibiting physiological activities, by introducing with at least one therapeutically effective modified nucleic acid. For example, in case of oligonucleotide sequences which are known to exhibit cell growth inhibition activities such as TTTGGTGGTGGTGGTTGTGGTGGTGGTGG (SEQ ID NO: 50) or GGTGGTGGTGGTTGTGGTGGTGGTGG (SEQ ID NO: 51), various novel modified oligonucleotides can be synthesized by introducing with at least one therapeutically effective modified nucleic acid, for example, 5-FdU ('F' hereafter) or 2',2'-difluorodeoycytidine/gemcitabine (Gemcitabine, 'Z' hereafter). More specifically, for example, by introducing a therapeutically effective modified nucleic acid at a suitable position of any of oligonucleotides having the above sequences including

| | |
|---|---|
| FFFGGFGGFGGFGGFFGFGGFGGFGGFGG, | (SEQ ID NO: 52) |
| FFFGGTGGTGGTGGTTGTGGTGGTGGTGG, | (SEQ ID NO: 53) |
| GGFGGFGGFGGFFGFGGFGGFGGFGG, | (SEQ ID NO: 54) |
| GGFGGFGGFGGFFFFGGFGGFGGFGG, | (SEQ ID NO: 55) |
| GGFGGFGGFGGTTGTGGFGGFGGFGG, | (SEQ ID NO: 56) |
| GGFGGFGGTGGTTGTGGTGGFGGFGG, | (SEQ ID NO: 57) |
| GGFGGTGGTGGTTGTGGTGGTGGFG, | (SEQ ID NO: 58) |
| GGTGGTGGTGGFFFFGGTGGTGGTGG, | (SEQ ID NO: 59) |
| GGTGGTGGTGGFFGFGGTGGTGGTGG, | (SEQ ID NO: 60) |
| GGZGGZGGZGGZZGZGGZGGZGGZGG, | (SEQ ID NO: 61) |
| GGTGGTGGTGGTTZTGGTGGTGGTGG, | (SEQ ID NO: 62) |
| GGTGGTGGTGGTZZTGGTGGTGGTGG, | (SEQ ID NO: 63) |

```
GGTGGTGGTGGTZGTGGTGGTGGTGG,     (SEQ ID NO: 64)

GGTGGTGGTGGTTGZGGTGGTGGTGG,     (SEQ ID NO: 65)

GGTGGTGGTGGTZGZGGTGGTGGTGG,     (SEQ ID NO: 66)

GGZGGTGGTGGTTGTGGTGGTGGZGG,     (SEQ ID NO: 67)
and

GGTGGZGGTGGTTGTGGTGGZGGTGG,     (SEQ ID NO: 68)
``` various novel modified nucleotides can be synthesized. These are also shown to have excellent cell apoptotic activity.

That is, novel modified oligonucleotides can be obtained by introducing with therapeutically effective modified nucleic acid of the present invention at a suitable position of any of oligonucleotides which were reported for the purpose of therapeutic treatment or those oligonucleotides with G-quadruplex structure having physiological activities.

The sequences of novel modified oligonucleotides and position for the introduction of modified nucleic acids may influence the affinity or specificity to target proteins having G-quadruplex region. Therefore, the sequences of novel oligonucleotides and position for the introduction of modified nucleic acids may be determined by the affinity or specificity to target proteins having G-quatruplex region. The availability of the modified oligonucleotides prepared according to the present invention may be determined by the physiological activities being exhibited by decisive factors such as the binding affinity or specificity to target proteins having G-quardruplex region.

The sequences of novel modified oligonucleotides to be applicable for the above method are as follows.

The present invention relates to an oligonucleotide sequence called 'GxHyNz', wherein G is guanosine or its derivative; H is a nucleic acid exclusive of guanosine; N is uridine- or cytidine-derived modified nucleic acid with therapeutic efficacies, wherein G, H, N are randomly arranged; x is an integer of 1-30, y is an integer of 0-30, z is an integer of 1-30, wherein the sum of (x+y+z) is not greater than 60.

The above therapeutically effective modified nucleic acid (N) is represented by formula 4 or 5 and resides in modified oligonucleotides.

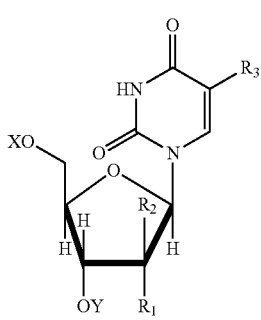

(4)

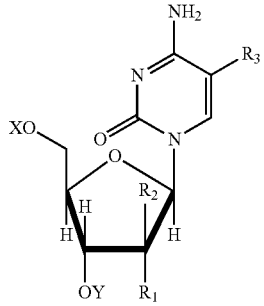

(5)

In the above formula 4 or 5, $R_1$ is a hydrogen, a halogen or a hydroxyl group, $R_2$ is a hydrogen, a halogen or a hydroxyl group, $R_3$ is a hydrogen, a halogen, $C_{1-10}$ alkyl, $C_{1-10}$ haloalkyl, $C_{2-10}$ alkenyl, $C_{2-10}$ haloalkenyl, wherein $R_1$, $R_2$ are not a hydroxyl group at the same time, X and Y are respectively is a hydrogen, or a phosphorous atom in the phosphate group of the adjoining nucleic acid.

The above H is more preferably adenosine, cytidine, uridine or thymidine, wherein the sum of (x+y+z) is in the range of 5-60, most preferably 14-26.

In the above, G is guanosine, preferably at least one selected from the group consisting of 2-deoxy-guanosine, guanosine, 2'-O-methyl-guanosine, 2'-F-guanosine, LNA (Locked Nucleic Acid)-guanosine, D-deoxyguanosine, and D-guanosine.

In the above, N is cytidine- or uridine-derived nucleic acid, preferably at least one selected from the group consisting of 5-fluorodeoxyuridine, 5-fluorouridine, 5-fluorodeoxycytidine, 5-fluorocytidine, 5-iododeoxyuridine, 5-iodouridine, 5-iododeoxycytidine, 5-iodocytidine, cytosine arabinoside/Ara-C, 2',2'-difluorodeoxycytidine/gemcitabine, capecitabine and bromovinyl-deoxyuridine. It may include a modified nucleic acid with a similar structure.

Conventional agents comprising therapeutically effective nucleoside are known to often cause side effects such as systemic toxicity and drug resistance. Further, many cancer cells are known to have resistance against these therapeutically effective nucleoside-containing anticancer agents thus requiring selection of other kinds of drugs instead. In case these therapeutically effective nucleosides are contained in an oligonucleotide with G-quadruplex structure, which tends to more selectively work on cancer cells, can minimize its influence on normal cells in the body, and also increase its cell apoptosis rate against drug-resistant cancers.

The above-mentioned modified oligonucleotide, as is the case of the oligonucleotide with G-quadruplex structure, has shown a minimum peak at about 240 nm, and the maximum peak at about 260-270 nm by circular dichroism (CD) analysis. These characteristic features support that the modified oligonucleotide of the present invention has the G-quadruplex structure, and relevant information has been reported (M. Lu, Q. Guo, N. R. Kallenback, Biochemistry, 1992, 31, 2455; P. Balagurumoorthy, S. K. Brahmachari, Nucleic Acids Res., 1992, 20, 4061; Proc. Natl. Acad. Sci. U.S.A. 91, 1994, 7658-7662; Biochemistry. 1997, 36, 12498; Biochemistry. 2002, 41, 3676).

The G-quadruplex structure becomes more stable in the presence of potassium ions ($K^+$). It maintains a stable structure in a physiological condition provided such as in blood for a relatively long period of time. Therefore, in the present invention, the oligonucleotide with G-quadruplex structure comprising modified therapeutically effective nucleic acid is stabilized before use by treating it with KCl solution (30-70 mM). The novel modified oligonucleotide according to the present invention showed that it has superior apoptotic effect over cancer cells to the clinical drug.

The present invention also relates to a pharmaceutical composition for preventing and treating cancer comprising the above modified oligonucleotide or its pharmaceutically acceptable salt as an active ingredient.

Examples of the pharmaceutically acceptable salt include a metal salt, a salt with an organic base, a salt with an inorganic acid, a salt with an organic acid, a salt with an acidic or basic amino acid, or the like.

Examples of the suitable metal salt include an alkali metal salt such as sodium salt and potassium salt; an alkali earth metal such as calcium salt, magnesium salt, and barium salt; aluminum salt, or the like.

Examples of the suitable salt with an organic base include a salt with trimethylamine, triethylamine, pyridine, picoline, 2,6-lutidine, ethanolamine, diethanolamine, triethanolamine, cyclohexylamine, di cyclohexylamine, N,N-dibenzylethyleneamine, or the like.

Examples of the suitable salt with an inorganic acid include a salt with hydrochloric acid, hydrobromic acid, nitric acid, sulfuric acid, phosphoric acid, or the like.

Examples of the suitable salt with an organic acid include a salt with formic acid, acetic acid, trifluoroacetic acid, phthalic acid, fumaric acid, oxalic acid, tartaric acid, maleic acid, citric acid, succinic acid, methane sulfonic acid, benzene sulfonic acid, p-toluene sulfonic acid, or the like.

Examples of the suitable salt with basic amino acid include a salt with alginine, lysine, ornithine, or the like.

Examples of the suitable salt with acidic amino acid include a salt with aspartic acid, glutamic acid, or the like.

In particular, examples of preferred salts, in case a compound has an acidic functional group in the compound are inorganic salts such as alkali metal salts (e.g., sodium salts, potassium salt, etc.) and alkali earth metal salts (e.g., calcium salt, magnesium salt, barium salt, etc.), and ammonium salt such as organic salts; and in case a compound has a basic functional group in the compound are a salt with an inorganic acid (e.g., hydrochloric acid, hydrobromic acid, nitric acid, sulfuric acid, phosphoric acid, etc.), and a salt with an organic salt (e.g., acetic acid, phthalic acid, fumaric acid, oxalic acid, tartaric acid, maleic acid, citric acid, succinic acid, methane sulfonic acid, p-toluene sulfonic acid, etc.).

The pharmaceutical composition for preventing and treating cancer comprising the above modified oligonucleotide may comprise a pharmaceutically acceptable carrier, in addition to an active ingredient. Examples of the pharmaceutically acceptable carrier, in case of an injection are a preservative, an isotonic agent, an anesthetic agent, a solubilizing agent, a buffer, etc., or a mixture thereof; in case of an oral administration are a solubilizing agent, a binder, a diluent, a dispersant, a stabilizer, a suspending agent, a color disintegrating agent, a lubricant, flavor, etc.; and in case of a local administration are a base, a diluent, a lubricant, a preservative, etc.

The preparation of the pharmaceutical composition of the present invention can be formulated into various types by mixing with a pharmaceutically acceptable carrier. Further, it can be prepared in the form of a unit dose ampoule or multiple dose form in case of an injection; prepared in the form of a tablet, an elixir, a capsule, suspension, trochey, wafer, syrup in case of an oral administration; and other forms including suspension, a tablet, a pill, a capsule and a preparation with suspended release, or the like.

Examples of carriers, excipients, and diluents suitable for the pharmaceutical preparations include microcrystalline cellulose, xylitol, erythritol, methyl cellulose, polyvinylpyrrolidone, starch, acacia, alginate, gelatin, lactose, dextrose, sucrose, propylhydroxybenzoate, cellulose, water, methylhydroxybenzoate, magnesium stearate, talc, sorbitol, mannitol, maltitol, calcium phosphate, calcium silicate, mineral oil, or the like.

In the present invention, "administration" refers to an introduction of a certain substance to a patient via any appropriate route. The administration route of an active ingredient is not limited but any administration route may be applied as long as it can serve to deliver a certain drug substance to a target tissue, for example, intravenous administration, subcutaneous administration, oral administration, intramuscular administration, intraperitoneal administration, intrapulmonary administration, rectal administration, local administration, intranasal administration, intradermal administration, but are not limited thereto. However, because oligonucleotides are digested when administered via oral administration, pharmaceutical composition for oral administration must be prepared so that it can be decomposed and absorbed in gastrointestinal tract. Preferably, it may be administered by injection or through an internasal route.

The content of the active ingredient of pharmaceutical preparations of the present invention may be suitably selected depending on the absorptivity of active ingredient, inactivation ratio, excretion rate, age of a user, sex, and health conditions, etc. In the present invention, the content of the active ingredient is 1-1000 mg/kg, preferably 100 mg/kg, and may be administered 1-3 times daily or administered continuously by infusion for a certain period of time.

The present invention is described hereunder but they should not be construed as limiting the scope of the present invention.

Example 1

Synthesis of Novel Modified Oligonucleotides

The novel modified oligonucleotides were synthesized using DNA synthesizer (Polygene, Inc.) in 1 µM scale with standard solid phase phosphoramidite chemistry. Deoxyguanosine, thymidine, deoxycytidine, 5-fluoro-deoxyuridine, Ara-C and TMP-5-fluoro-deoxyuridine-phosphoramidite were purchased from Glen research Corporation, which were then dissolved in dry acetonitrile to a concentration of 0.067M, and loaded into the solid phase DNA synthesizer.

DNA was synthesized in 3'→5' direction to prepare the oligonucleotides whose sequences are shown in Table 1 below. With the 3'-OH of the first nucleotide being adhered to resin, a four-step chemical reaction comprising 5'-terminus detrytilation, a coupling of a new base, capping of uncoupled DNA chain, and oxidation of phosphate group was repeated while a base is being added. Upon completion of the reaction, the protector was removed. Thus synthesized CPG resin was added into an ammonia solution, left at 55° C. for 5 hours. Then, ammonia solution was dried to finally obtain white powdered product. The resultant was purified by using Waters cation exchange HPLC column wherein the concentration of 1M NaCl was increased to 5-70%. Then, main peaks were collected and added with 100% ethanol to precipitate oligonucleotides, which were dried thereafter. Thus obtained oligonucleotides were analyzed by HPLC and found to have a purity of greater than 85%. Their molecular weight was measured by using ESI-LC-MS (Q-TRAP 2000 ESI-MS) to determine the success of the synthesis.

Modified oligonucleotides can be synthesized by using the above method for the oligonucleotide sequences which were already reported for the purpose of therapeutic treatment or various sequences which exhibit physiological activities forming G-quadruplex structure in addition to the sequences shown in the following Table 1.

TABLE 1

| Comp. No. | N | G | H | Sequence | LC/MS |
|---|---|---|---|---|---|
| APT-2001 | 5-F-deoxyuridine | 2-deoxy-guanosine | — | NNNGGNGGNGGNGGNNGNGGNGGNGNGG (SEQ. ID. NO. 1) | 9232.53 |
| APT-2001B | 5-F-deoxycytidine | 2-deoxy-guanosine | — | NNNGGNGGNGGNGGNNGNGGNGGNGNGG (SEQ. ID. NO. 1) | 9220.77 |
| APT-2002 | 5-F-deoxyuridine | 2-deoxy-guanosine | thymidine | NNNGGTGGTGGTGGTTGTGGTGGTGGTGG (SEQ. ID. NO. 2) | 9196.89 |
| APT-2002B | 5-F-deoxycytidine | 2-deoxy-guanosine | thymidine | NNNGGTGGTGGTGGTTGTGGTGGTGGTGG (SEQ. ID. NO. 2) | 9193.95 |
| APT-2003 | 5-F-deoxyuridine | 2-deoxy-guanosine | thymidine | GGTGGTGGTGGTTGTGGTGGTGGTGGNNNG (SEQ. ID. NO. 3) | 9526.1 |
| APT-2003B | Cytosine arabinoside | 2-deoxy-guanosine | thymidine | GGTGGTGGTGGTTGTGGTGGTGGTGGNNNG (SEQ. ID. NO. 3) | 9517.16 |
| APT-2003C | 5-F-deoxycytidine | 2-deoxy-guanosine | thymidine | GGTGGTGGTGGTTGTGGTGGTGGTGGNNNG (SEQ. ID. NO. 3) | 9523.16 |
| APT-2004 | 5-F-deoxyuridine | 2-deoxy-guanosine | — | GGNGGNGGNGGNNGNGGNGGNGGNGG (SEQ. ID. NO. 4) | 8308.1 |
| APT-2005 | 5-F-deoxyuridine | 2-deoxy-guanosine | — | GGNGGNGGNGGNNNNGGNGGNGGNGG (SEQ. ID. NO. 5) | 8287 |
| APT-2007 | 5-F-deoxyuridine | 2-deoxy-guanosine | — | GGGNNNNGGGNNNNGGGNNNNGGG (SEQ. ID. NO. 6) | 7586.6 |
| APT-2008 | 5-F-deoxyuridine | 2-deoxy-guanosine | — | GGNGGNNNNGGNGG (SEQ. ID. NO. 7) | 4420.7 |
| APT-2009 | 5-F-deoxyuridine | 2-deoxy-guanosine | — | GGNGGNGGNGG (SEQ. ID. NO. 8) | 3496.2 |
| APT-2010 | 5-F-deoxyuridine | 2-deoxy-guanosine | — | GGNNNNGG (SEQ. ID. NO. 9) | 2487 |
| APT-2011 | 5-iodo-deoxyuridine | 2-deoxy-guanosine | — | NNNGGNGGNGGNGGNNGNGGNGGNGNGG (SEQ. ID. NO. 1) | 10799.4 |
| APT-2012 | Cytosine arabinoside | 2-deoxy-guanosine | — | NNNGGNGGNGGNGGNNGNGGNGGNGNGG (SEQ. ID. NO. 1) | 9468.76 |
| APT-2013 | 5-F-deoxyuridine | 2-deoxy-guanosine | thymidine | NNNGGNGGNGGNGGTTGTGGNGGNGNGG (SEQ. ID. NO. 10) | 9220.7 |
| APT-2014 | 5-F-deoxyuridine | 2-deoxy-guanosine | thymidine | NNNGGTGGTGGTGGNNGNGGTGGTGGTGG (SEQ. ID. NO. 11) | 9208.8 |
| APT-2015 | 5-F-deoxyuridine | 2-deoxy-guanosine | thymidine | GGNGGNGGNGGTTTTGGNGGNGGNGG (SEQ. ID. NO. 12) | 8271.2 |
| APT-2015B | 5-F-deoxyuridine | 2-deoxy-guanosine | 2'-deoxycytidine | GGNGGNGGNGGCCCCGGNGGNGGNGG (SEQ. ID. NO. 13) | 8211.08 |

TABLE 1-continued

| Comp. No. | N | G | H | Sequence | LC/MS |
|---|---|---|---|---|---|
| APT-2015C | Cytosine arabinoside | 2-deoxy-guanosine | thymidine | GGNGGNGGNGGCCCCGGNGGNGGNGG (SEQ. ID. NO. 13) | 8193.10 |
| APT-2016 | 5-F-deoxyuridine | 2-deoxy-guanosine | thymidine | GGTGGTGGTGGNNNNGGTGGTGGTGG (SEQ. ID. NO. 14) | 8263.2 |
| APT-2017 | 5-F-deoxyuridine | 2-deoxy-guanosine | thymidine | GGNGGNGGNGGNNNNGGTGGTGGTGG (SEQ. ID. NO. 15) | 8275.1 |
| APT-2018 | 5-F-deoxyuridine | 2-deoxy-guanosine | thymidine | GGTGGTGGTGGNNNNGGNGGNGGNGG (SEQ. ID. NO. 16) | 8275.1 |
| APT-2019 | 5-F-deoxyuridine | 2-deoxy-guanosine | thymidine | GGNGGNGGTTTTGGNGGNGG (SEQ. ID. NO. 17) | 6338 |
| APT-2019B | Cytosine arabinoside | 2-deoxy-guanosine | thymidine | GGTGGTGGNNNNGGTGGTGG (SEQ. ID. NO. 18) | 6326.08 |
| APT-2020 | 5-F-deoxyuridine | 2-deoxy-guanosine | thymidine | GGTGGTGGNNNNGGTGGTGG (SEQ. ID. NO. 18) | 6338 |
| APT-2021 | 5-F-deoxyuridine | 2-deoxy-guanosine | thymidine | GGNGGTTTTGGNGG (SEQ. ID. NO. 19) | 4404.8 |
| APT-2022 | 5-F-deoxyuridine | 2-deoxy-guanosine | thymidine | GGTGGNNNNGGTGG (SEQ. ID. NO. 20) | 4412.8 |
| APT-2023 | 5-F-deoxyuridine | 2-deoxy-guanosine | thymidine | GGNGGTGGNGG (SEQ. ID. NO. 21) | 3492.2 |
| APT-2024 | 5-F-deoxyuridine | 2-deoxy-guanosine | thymidine | GGTNNTGG (SEQ. ID. NO. 22) | 2479.6 |
| APT-2025 | 2',2'-difluoro deoxycytidine | 2-deoxy-guanosine | — | GGNGGNGGNGGNNGNGGNGGNGGNGG (SEQ. ID. NO. 4) | 8461.2 |
| APT-2026 | 2',2'-difluoro deoxycytidine | 2-deoxy-guanosine | thymidine | GGGNNNNGGGNNNNGGGNNNNGGG (SEQ. ID. NO. 6) | 7790.7 |
| APT-2027 | 2',2'-difluoro deoxycytidine | 2-deoxy-guanosine | thymidine | GGNGGNNNNGGNGG (SEQ. ID. NO. 7) | 4522.8 |
| APT-2028 | Cytosine arabinoside | 2-deoxy-guanosine | — | GGNGGNGGNGGNNGNGGNGGNGGNGG (SEQ. ID. NO. 4) | 8281.2 |
| APT-2030 | Cytosine arabinoside | 2-deoxy-guanosine | — | GGNGGNNNNGGNGG (SEQ. ID. NO. 7) | 4402.8 |
| APT-2031 | 5-F-deoxyuridine | 2-deoxy-guanosine | thymidine | GGTGGTGGTNNTGGTGGTGG (SEQ. ID. NO. 23) | 6326 |
| APT-2032 | 5-F-deoxyuridine | 2-deoxy-guanosine | thymidine | GGTGGTGGTTNTGGTGGTGG (SEQ. ID. NO. 24) | 6324.1 |
| APT-2033 | 5-F-deoxyuridine | 2-deoxy-guanosine | thymidine | GGTGGTGGTTTNGGTGGTGG (SEQ. ID. NO. 25) | 6324.1 |
| APT-2034 | 5-F-deoxyuridine | 2-deoxy-guanosine | thymidine | GGTGGTGGTNNNGGTGGTGG (SEQ. ID. NO. 26) | 6328 |
| APT-2035 | 2',2'-difluoro deoxycytidine | 2-deoxy-guanosine | thymidine | GGTGGTGGTTNTGGTGGTGG (SEQ. ID. NO. 24) | 6343.1 |
| APT-2037 | 5-F-deoxyuridine | 2-deoxy-guanosine | thymidine | GGTGGTGGTGGNGNGGTGGTGGTGG (SEQ. ID. NO. 27) | 8284.3 |
| APT-2038 | 5-F-deoxyuridine | 2-deoxy-guanosine | thymidine | GGTGGTGGTGGTNNNGGTGGTGGTGG (SEQ. ID. NO. 28) | 8259.3 |
| APT-2039 | 5-F-deoxyuridine | 2-deoxy-guanosine | thymidine | GGTGGTGGTGGTNNTGGTGGTGGTGG (SEQ. ID. NO. 29) | 8255.3 |

TABLE 1-continued

| Comp. No. | N | G | H | Sequence | LC/MS |
|---|---|---|---|---|---|
| APT-2040 | 5-F-deoxyuridine | 2-deoxy-guanosine | thymidine | GGTGGTGGTGGTTNTGGTGGTGGTGG (SEQ. ID. NO. 30) | 8251.3 |
| APT-2041 | 5-F-deoxyuridine | 2-deoxy-guanosine | thymidine | GGTGGTGGTGGTTGNGGTGGTGGTGG (SEQ. ID. NO. 31) | 8276.3 |
| APT-2042 | 5-F-deoxyuridine | 2-deoxy-guanosine | thymidine | GGNGGNGGNGGTTGTGGNGGNGGNGG (SEQ. ID. NO. 32) | 8296.3 |
| APT-2043 | 5-F-deoxyuridine | 2-deoxy-guanosine | thymidine | GGNGGNGGTGGTTGTGGTGGNGGNGG (SEQ. ID. NO. 33) | 8288.3 |
| APT-2044 | 5-F-deoxycytidine | 2-deoxy-guanosine | thymidine | GGNGGTGGTGGTTGTGGTGGTGGNGG (SEQ. ID. NO. 34) | 8280.3 |
| APT-2050 | 2',2'-difluoro deoxycytidine | 2-deoxy-guanosine | thymidine | NNGGTGGTGGTGGTTGTGGTGGTGGTGG (SEQ. ID. NO. 35) | 8922.7 |
| APT-2051 | 2',2'-difluoro deoxycytidine | 2-deoxy-guanosine | thymidine | NGGTGGTGGTGGTTGTGGTGGTGGTG G (SEQ. ID. NO. 36) | 8597.5 |
| APT-2054 | 2',2'-difluoro deoxycytidine | 2-deoxy-guanosine | thymidine | GGTGGTGGTGGTTNTGGTGGTGGTGG (SEQ. ID. NO. 30) | 8268 |
| APT-2059 | 2',2'-difluoro deoxycytidine | 2-deoxy-guanosine | thymidine | GGTGGTGGTNNTGGTGGTGG (SEQ. ID. NO. 23) | 6364.1 |
| APT-2060 | 2',2'-difluoro deoxycytidine | 2-deoxy-guanosine | thymidine | GGTGGTGGNTGTGGTGGTGG (SEQ. ID. NO. 37) | 6368.1 |
| APT-2061 | 2',2'-difluoro deoxycytidine | 2-deoxy-guanosine | thymidine | GGTGGTGGTNGTGGTGGTGG (SEQ. ID. NO. 38) | 6368.1 |
| APT-2062 | 2',2'-difluoro deoxycytidine | 2-deoxy-guanosine | thymidine | GGTGGTGGTTGNGGTGGTGG (SEQ. ID. NO. 39) | 6368.1 |
| APT-2063 | 2',2'-difluoro deoxycytidine | 2-deoxy-guanosine | thymidine | GGTGGTGGTNGNGGTGGTGG (SEQ. ID. NO. 40) | 6389.1 |
| APT-2064 | 2',2'-difluoro deoxycytidine | 2-deoxy-guanosine | thymidine | GGNGGTGGTTGTGGTGGNGG (SEQ. ID. NO. 41) | 6389.1 |
| APT-2065 | 2',2'-difluoro deoxycytidine | 2-deoxy-guanosine | thymidine | GGTGGNGGTTGTGGNGGTGG (SEQ. ID. NO. 42) | 6389.1 |
| APT-2066 | 2',2'-difluoro deoxycytidine | 2-deoxy-guanosine | thymidine | GGTGGTGGTGGTNNTGGTGGTGGTGG (SEQ. ID. NO. 29) | 8289.3 |
| APT-2067 | 2',2'-difluoro deoxycytidine | 2-deoxy-guanosine | thymidine | GGTGGTGGTGGTNGTGGTGGTGGTGG (SEQ. ID. NO. 43) | 8293.3 |
| APT-2068 | 2',2'-difluoro deoxycytidine | 2-deoxy-guanosine | thymidine | GGTGGTGGTGGTTGNGGTGGTGGTGG (SEQ. ID. NO. 31) | 8293.3 |
| APT-2069 | 2',2'-difluoro deoxycytidine | 2-deoxy-guanosine | thymidine | GGTGGTGGTGGTNGNGGTGGTGGTGG (SEQ. ID. NO. 44) | 8314.3 |
| APT-2070 | 2',2'-difluoro deoxycytidine | 2-deoxy-guanosine | thymidine | GGNGGTGGTGGTTGTGGTGGTGGTGG (SEQ. ID. NO. 45) | 8314.3 |
| APT-2071 | 2',2'-difluoro deoxycytidine | 2-deoxy-guanosine | thymidine | GGTGGNGGTGGTTGTGGTGGNGGTGG (SEQ. ID. NO. 46) | 8314.3 |
| APT-2072 | 2',2'-difluoro deoxycytidine | 2-deoxy-guanosine | thymidine | GGTGGTGGTTNTGGTGGTGGN (SEQ. ID. NO. 47) | 6668.3 |
| APT-4001 (Pos. Cont.) | — | 2-deoxy-guanosine | thymidine | TTTGGTGGTGGTGGTTGTGGTGGTGGT GG (SEQ. ID. NO. 48) | 9185.01 |

TABLE 1-continued

| Comp. No. | N | G | H | Sequence | LC/MS |
|---|---|---|---|---|---|
| APT-4002 (Neg. Cont.) | — | — | thymidine, 2'-deoxycytidine | TTTCCTCCTCCTCCTTCTCCTCCTCCTC C (SEQ. ID. NO. 49) | 8504.5 |

Example 2

Synthesis of Modified Oligonucleotides

Each oligonucleotide was diluted in 10 mM Tris-HCl (pH 7.4) to a final concentration of 100 μM. The diluted solution was placed at 94° C. for 5 minutes and then quickly placed them on ice and left therein for 5 minutes. The resultant was added with 2M KCl to a final concentration of 50 mM, left at 60° C. for 3 hours and then slowly cooled down to room temperature.

Experimental Example 1

Measurement of Cell Apoptosis in Cancer Cells

One day before the experiment, 190 μL of culture, wherein PC-3 cell line(prostate cancer cell) was suspended at a concentration of $10^3$-$10^4$/mL, was inoculated respectively into each well of a 96 well plate. The next day, 10 μL of the oligonucleotide solution prepared in Example 1 was added and cultured for six days. Six days after the inoculation, cell apoptosis rate measured by means of XTT method [JBC 1999, 26369].

Figure 2:
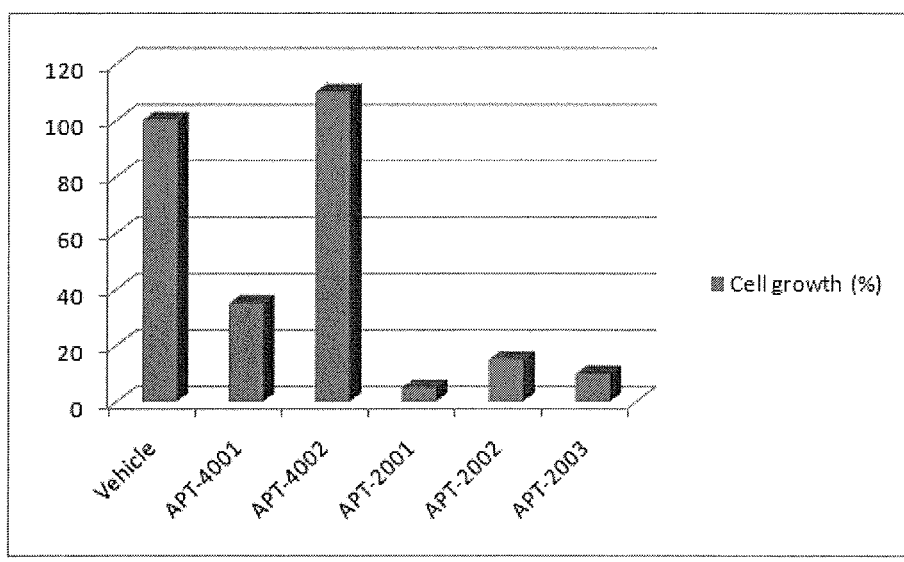
FIG. 2 shows the level of cell growth inhibition by various modified oligonucleotides.
Figure 3:
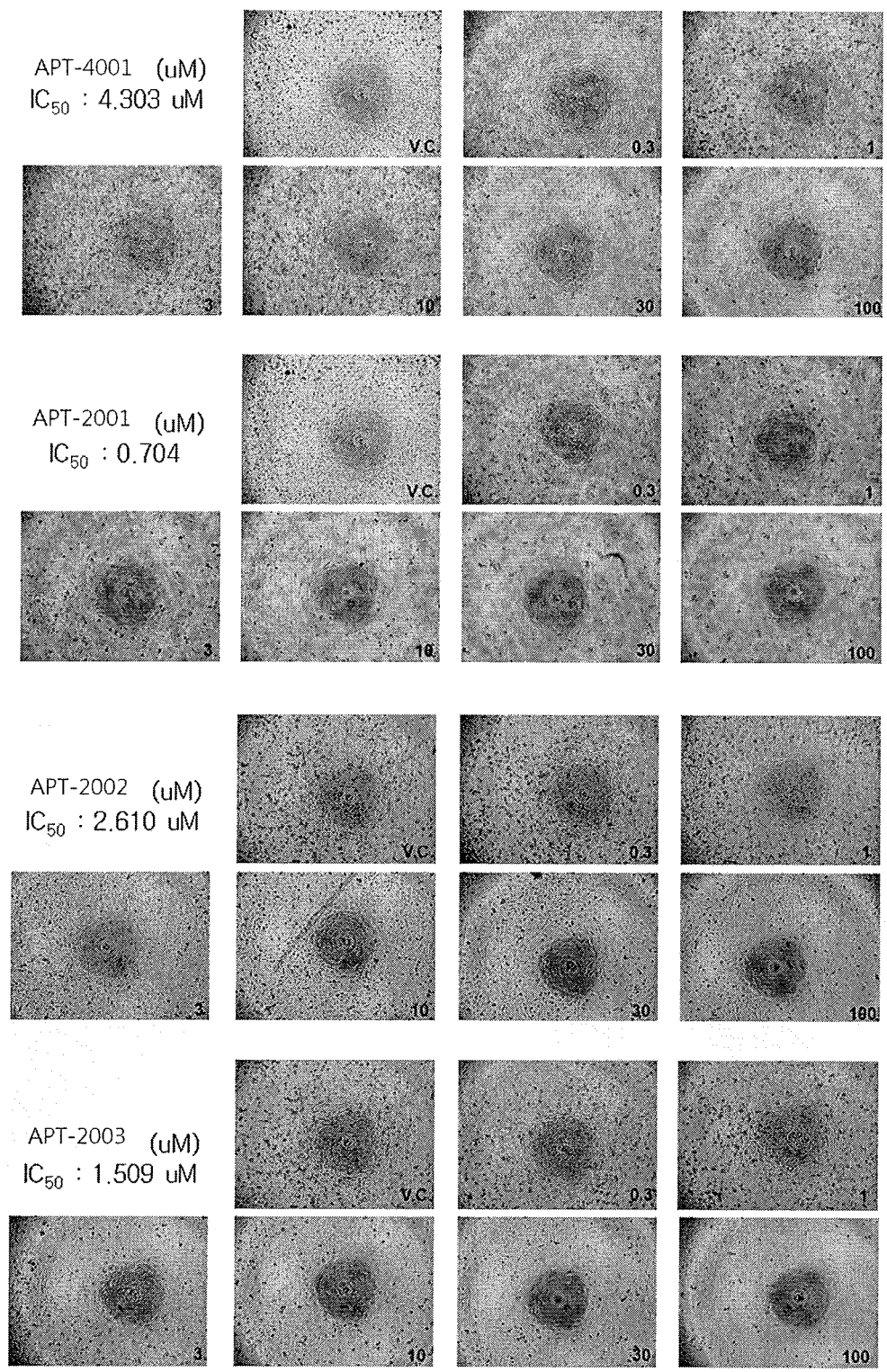
FIG. 3 shows pictures at $IC_{50}$ of each modified oligonucleotide and the cell morphology thereof.
Figure 4:
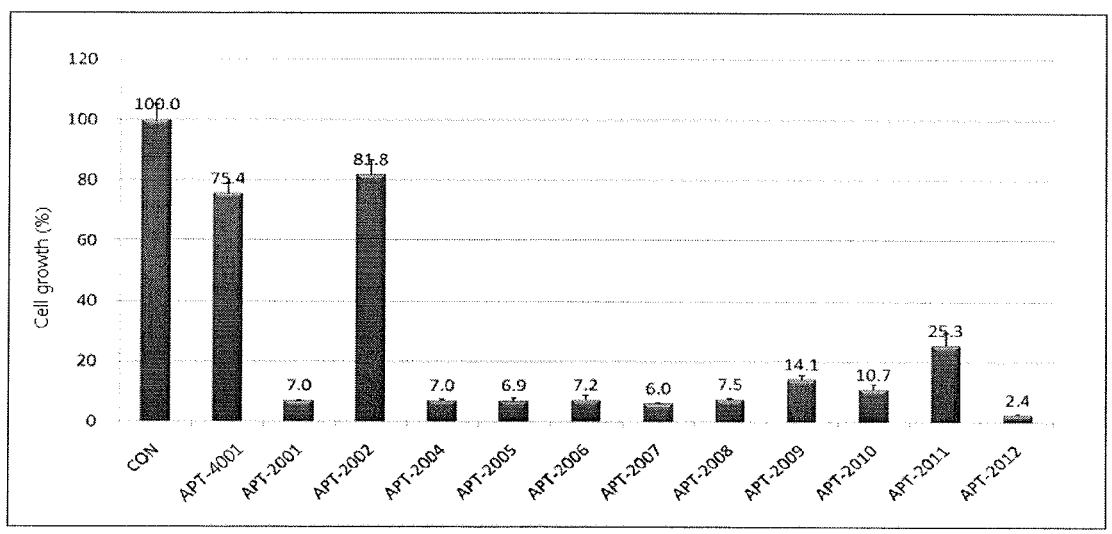
FIG. 4 is a graph showing the comparative cell apoptotic activities of various modified oligonucleotides against K562 CML cells (chronic myeloid leukemia) (Cell growth %, in 1 μM)
Figure 5:
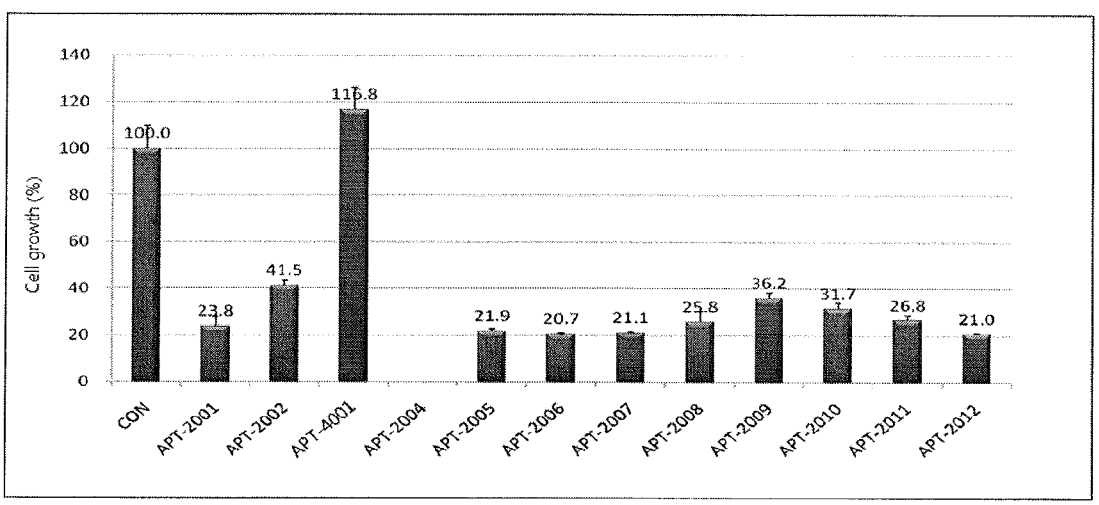
FIG. 5 is a graph showing the comparative cell apoptotic activities of various modified oligonucleotides against MV-4-11 AML cells (acute leukemia) (Cell growth %, in 2 μM)

As a result, it was confirmed that the cell apoptosis rate of APT-2001, APT-2002 and APT-2003 (the novel modified oligonucleotides of the present invention), was 3-10 times higher than those of APT-4001 (positive control) and APT-4002 (negative control) as measured in terms of $IC_{50}$ or $IC_{90}$ (FIG. 2). Besides, APT-2001, APT-2002 and APT-2003, even at a smaller amount as compared to that of APT-4001 (positive control), showed superior cell apoptotic activity (FIG. 3). Further, other novel oligonucleotides prepared according to the present invention were shown to have excellent cell apoptotic activity. In fact, they exhibited excellent cell apoptotic activity over various cancer cell lines including PC3, MCF7, HCT116, A549, A498, K562, MV-4-11, etc., thus confirming that they have a broad spectrum of anticancer activity. In particular, they also showed excellent anticancer activity against MCF7-DX, a drug-resistance cell line. The above-mentioned cell apoptotic activity is shown in Tables 2-7. In addition, the cell apoptotic activity of the oligonucleotides, prepared according to the present invention over the K562 CML (chronic myeloid leukemia), MV-4-11 AML (acute leukemia) cells, were also verified. The results are shown in FIGS. 4 and 5, respectively.

TABLE 2

| PC3 (Prostate Cancer Cells) | |
|---|---|
| SEQ. ID. NO. | $IC_{50}$ (μM) |
| APT-2001 | 0.7 |
| APT-2002 | 2.6 |
| APT-2003 | 1.5 |
| APT-2013 | 0.09 |
| APT-2020 | 0.16 |

TABLE 2-continued

| PC3 (Prostate Cancer Cells) | |
|---|---|
| SEQ. ID. NO. | $IC_{50}$ (μM) |
| APT-2022 | 0.11 |
| APT-2023 | 0.26 |
| APT-2031 | >10 |
| APT-2032 | >10 |
| APT-2033 | >10 |
| APT-2034 | >10 |
| APT-2035 | 0.035 |
| APT-2036 | 9.9 |
| APT-2054 | <0.3 |
| APT-2059 | 0.015 |
| APT-2060 | 0.04 |
| APT-2061 | 0.041 |
| APT-2063 | 0.022 |
| APT-2064 | 0.016 |
| APT-2066 | 0.034 |
| APT-2070 | 0.024 |
| APT-2072 | 0.012 |
| APT-4001 | 4.3-7.4 |
| APT-4002 | >50 |

TABLE 3

| MCF7-DX (Breast Cancer Cells) | |
|---|---|
| SEQ. ID. NO. | $IC_{50}$ (μM) |
| APT-2001 | 0.2 |
| APT-2002 | 0.6 |
| APT-2013 | 0.66 |
| APT-2020 | 0.89 |
| APT-2022 | 0.79 |
| APT-2023 | 1.86 |
| APT-2031 | 1.5 |
| APT-2032 | 3.6 |
| APT-2033 | 3.3 |
| APT-2034 | 1.2 |
| APT-2035 | 0.007 |
| APT-2036 | 0.2 |
| APT-2040 | >1.0 |
| APT-2042 | 0.5 |
| APT-2043 | 0.6 |
| APT-2044 | >1.0 |
| APT-2054 | <0.3 |
| APT-2059 | 0.004 |
| APT-2060 | 0.023 |
| APT-2061 | 0.022 |
| APT-2063 | 0.008 |
| APT-2064 | 0.008 |
| APT-2066 | 0.01 |
| APT-2067 | 0.024 |
| APT-2068 | 0.023 |
| APT-2069 | 0.01 |
| APT-2070 | 0.013 |
| APT-2071 | 0.015 |
| APT-4001 | >30 |
| APT-4002 | >50 |

TABLE 4

MCF7 (Breast Cancer Cells)

| SEQ. ID. NO. | IC$_{50}$ (μM) |
| --- | --- |
| APT-2001 | 2.1 |
| APT-2002 | 8.9 |
| APT-4001 | 7.3 |
| APT-4002 | NA |

TABLE 5

HCT116 (Rectal Cancer Cells)

| SEQ. ID. NO. | IC$_{50}$ (μM) |
| --- | --- |
| APT-2001 | 0.4 |
| APT-2002 | 2.1 |
| APT-4001 | >30 |
| APT-4002 | >50 |

TABLE 6

A549 (Non-small Cell Carcinoma Cells)

| SEQ. ID. NO. | IC$_{50}$ (μM) |
| --- | --- |
| APT-2001 | 0.9 |
| APT-2002 | 5.2 |
| APT-4001 | 3.7 |
| APT-4002 | >50 |

TABLE 7

A498 (Kidney Cancer Cells)

| SEQ. ID. NO. | IC$_{50}$ (μM) |
| --- | --- |
| APT-2001 | <0.1 |
| APT-2002 | <0.1 |
| APT-4001 | 1.9 |
| APT-4002 | >50 |

Experimental Example 2

Confirmation of G-Quadruplex Formation

The formation of G-quadruplex structure in the oligonucleotides prepared in the above Example 1 was examined by using CD (Circular dichroism) analysis. The oligonucleotide solutions prepared in Example 1 were respectively diluted in 10 mM potassium phosphate buffer to a final concentration of 1 mM and stored in a freezer. Each oligonucleotide was diluted in 10 mM potassium phosphate buffer to a final concentration of 100 μM to obtain a 2 mL solution, and analyzed by CD (Circular dichroism) analysis. CD spectra was observed by using JARSCO J-810 spectropolarimeter at 20° C. in the range of 320 nm-220 nm, with 100 nm/min scan speed, 0.5 s response time, 2 nm band width, 1 cm path length.

As a result, it was shown that there was a maximum peak at 264 nm, and also it was confirmed that it exhibited the same CD spectrum as that of APT-4001, a positive control known to form G-quadruplex structure.

Figure 6:
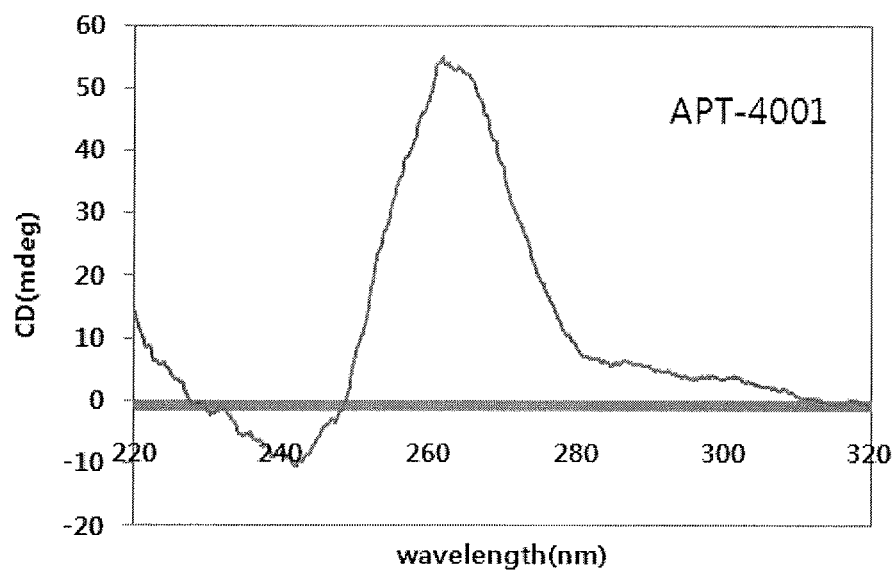
FIG. 6 is a graph showing the result of circular dichroism (CD) analysis to confirm the presence of G-quadruplex structure in APT-4001 oligonucleotide, a positive control.
Figure 7:
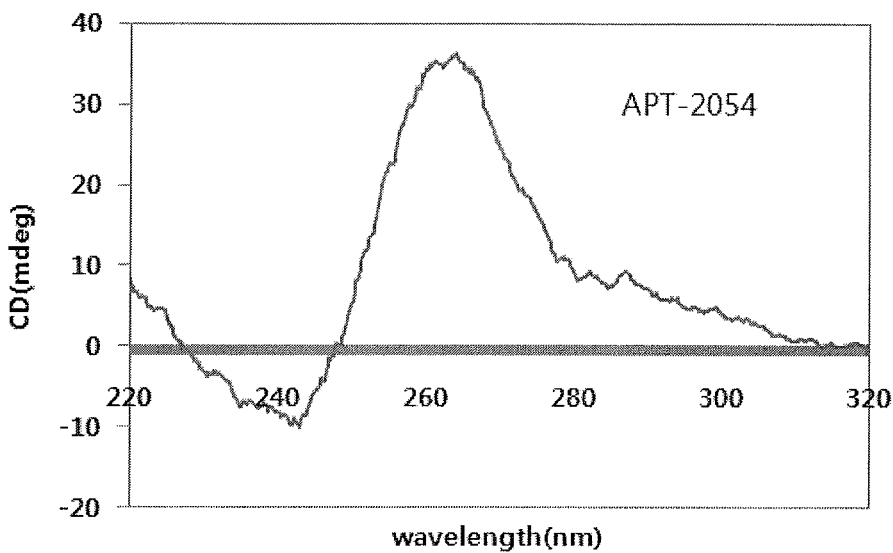
FIG. 7 is a graph showing the result of circular dichroism (CD) analysis to confirm the presence of G-quadruplex structure in APT-2054 oligonucleotide prepared in Example 1.
Figure 8:
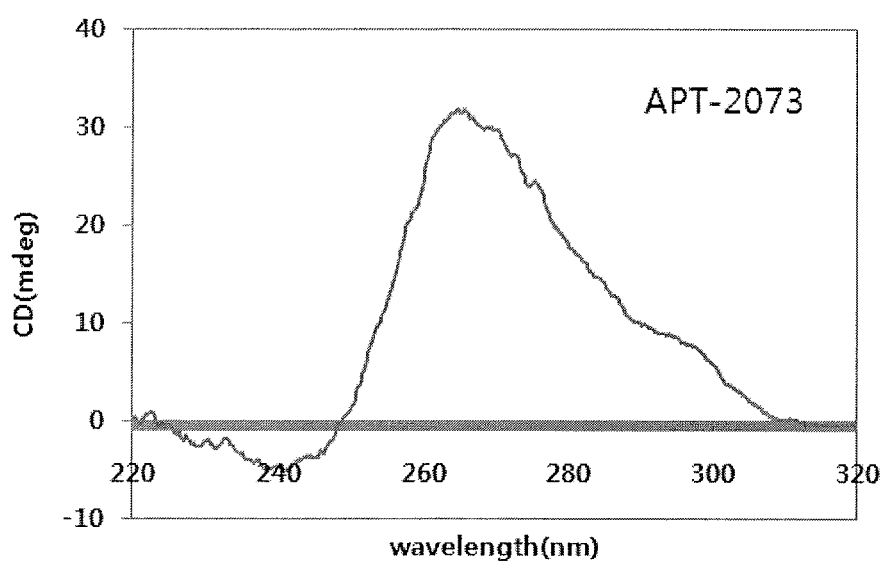
FIG. 8 is a graph showing the result of circular dichroism (CD) analysis to confirm the presence of G-quadruplex structure in APT-2073 oligonucleotide prepared in Example 1.

From the foregoing, it was confirmed that the modified oligonucleotides of the present invention form G-quadruplex structure, as disclosed in related art on formation of G-quadruplex structure (M. Lu, Q. Guo, N. R. Kallenback, Biochemistry, 1992, 31, 2455; P. Balagurumoorthy, S. K. Brahmachari, Nucleic Acids Res., 1992, 20, 4061; Proc. Natl. Acad. Sci. U.S.A. 91, 1994, 7658-7662; Biochemistry. 1997, 36, 12498; Biochemistry. 2002, 41, 3676) [FIGS. 6-8].

Experimental Example 3

Toxicity Test

Toxicity test was performed on the active ingredient of the present invention as follows.

Each of APT-2001, APT-2002 and APT-2003 was dissolved in dimethylsulfoxide (DMSO), diluted with water and then administered to mice (10 mice/group) in the amount of 1 g/kg. The mice were observed for the next 7 days and confirmed that all mice survived.

Preparation Example 1

Preparation of Injection Fluid

Injection fluid containing 10 mg of APT-2001 was prepared as follows.

1 g of APT-2001, 0.6 g of sodium chloride, and 0.1 g of ascorbic acid were dissolved in distilled water to a final volume of 100 mL. The mixture was added into a vial and sterilized by heating at 20° C. for 30 minutes.

| (Formulation of Injection Fluid) | |
| --- | --- |
| Active Ingredient | 1 g |
| Sodium Chloride | 0.6 g |
| Ascorbic Acid | 0.1 g |
| Distilled Water | Adequate Amount |

The invention claimed is:

1. A modified oligonucleotide with a G-quadruplex structure indicated by nucleotide sequence 'GxHyNz', wherein said modified oligonucleotide is selected from the group consisting of SEQ ID NOs. 1-47.

2. A pharmaceutical composition for preventing or treating cancer comprising the modified oligonucleotide according to claim 1 or its pharmaceutically acceptable salt thereof as active ingredient.

* * * * *

SEQUENCE LISTING

```
<160> NUMBER OF SEQ ID NOS: 68

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 5-F-deoxyuridine, 5-F-deoxycytidine,
```

```
    5-iodo-deoxyuridine or Cytosine arabinoside
<220> FEATURE:
<221> NAME/KEY: modified_base
<222> LOCATION: (6)..(6)
<223> OTHER INFORMATION: 5-F-deoxyuridine, 5-F-deoxycytidine,
      5-iodo-deoxyuridine or Cytosine arabinoside
<220> FEATURE:
<221> NAME/KEY: modified_base
<222> LOCATION: (9)..(9)
<223> OTHER INFORMATION: 5-F-deoxyuridine, 5-F-deoxycytidine,
      5-iodo-deoxyuridine or Cytosine arabinoside
<220> FEATURE:
<221> NAME/KEY: modified_base
<222> LOCATION: (12)..(12)
<223> OTHER INFORMATION: 5-F-deoxyuridine, 5-F-deoxycytidine,
      5-iodo-deoxyuridine or Cytosine arabinoside
<220> FEATURE:
<221> NAME/KEY: modified_base
<222> LOCATION: (15)..(16)
<223> OTHER INFORMATION: 5-F-deoxyuridine, 5-F-deoxycytidine,
      5-iodo-deoxyuridine or Cytosine arabinoside
<220> FEATURE:
<221> NAME/KEY: modified_base
<222> LOCATION: (18)..(18)
<223> OTHER INFORMATION: 5-F-deoxyuridine, 5-F-deoxycytidine,
      5-iodo-deoxyuridine or Cytosine arabinoside
<220> FEATURE:
<221> NAME/KEY: modified_base
<222> LOCATION: (21)..(21)
<223> OTHER INFORMATION: 5-F-deoxyuridine, 5-F-deoxycytidine,
      5-iodo-deoxyuridine or Cytosine arabinoside
<220> FEATURE:
<221> NAME/KEY: modified_base
<222> LOCATION: (24)..(24)
<223> OTHER INFORMATION: 5-F-deoxyuridine, 5-F-deoxycytidine,
      5-iodo-deoxyuridine or Cytosine arabinoside
<220> FEATURE:
<221> NAME/KEY: modified_base
<222> LOCATION: (27)..(27)
<223> OTHER INFORMATION: 5-F-deoxyuridine, 5-F-deoxycytidine,
      5-iodo-deoxyuridine or Cytosine arabinoside
<220> FEATURE:
<221> NAME/KEY: misc_feature
<222> LOCATION: (1)..(29)
<223> OTHER INFORMATION: All "n's" are defined the same (i.e. if "n" is
      defined as 5-F-deoxyuridine, then all "n's" are defined as
      5-F-deoxyuridine)
<220> FEATURE:
<221> NAME/KEY: misc_feature
<222> LOCATION: (1)..(29)
<223> OTHER INFORMATION: If "n's" are defined as "u's", the sequence
      would be described as an artificial combined molecule

<400> SEQUENCE: 1
nnnggnggng gnggnngngg nggnggngg                                           29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 5-F-deoxyuridine or 5-F-deoxycytidine
<220> FEATURE:
<221> NAME/KEY: misc_feature
<222> LOCATION: (1)..(29)
<223> OTHER INFORMATION: All "n's" are defined the same (i.e. if "n" is
      defined as 5-F-deoxyuridine, then all "n's" are defined as
      5-F-deoxyuridine)
<220> FEATURE:
<221> NAME/KEY: misc_feature
<222> LOCATION: (1)..(29)
<223> OTHER INFORMATION: If "n's" are defined as "u's", the sequence
``` would be described as an artificial combined molecule

<400> SEQUENCE: 2
nnnggtggtg gtggttgtgg tggtggtgg                                               29

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(29)
<223> OTHER INFORMATION: 5-F-deoxyuridine, Cytosine arabinoside
      or 5-F-deoxycytidine
<220> FEATURE:
<221> NAME/KEY: misc_feature
<222> LOCATION: (1)..(30)
<223> OTHER INFORMATION: All "n's" are defined the same (i.e. if "n" is
      defined as 5-F-deoxyuridine, then all "n's" are defined as
      5-F-deoxyuridine)
<220> FEATURE:
<221> NAME/KEY: misc_feature
<222> LOCATION: (1)..(30)
<223> OTHER INFORMATION: If "n's" are defined as "u's", the sequence
      would be described as an artificial combined molecule

<400> SEQUENCE: 3
ggtggtggtg gttgtggtgg tggtggnnng                                              30

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-F-deoxyuridine or 2',2'-difluorodeoxycytidine
<220> FEATURE:
<221> NAME/KEY: modified_base
<222> LOCATION: (6)..(6)
<223> OTHER INFORMATION: 5-F-deoxyuridine or 2',2'-difluorodeoxycytidine
<220> FEATURE:
<221> NAME/KEY: modified_base
<222> LOCATION: (9)..(9)
<223> OTHER INFORMATION: 5-F-deoxyuridine or 2',2'-difluorodeoxycytidine
<220> FEATURE:
<221> NAME/KEY: modified_base
<222> LOCATION: (12)..(13)
<223> OTHER INFORMATION: 5-F-deoxyuridine or 2',2'-difluorodeoxycytidine
<220> FEATURE:
<221> NAME/KEY: modified_base
<222> LOCATION: (15)..(15)
<223> OTHER INFORMATION: 5-F-deoxyuridine or 2',2'-difluorodeoxycytidine
<220> FEATURE:
<221> NAME/KEY: modified_base
<222> LOCATION: (18)..(18)
<223> OTHER INFORMATION: 5-F-deoxyuridine or 2',2'-difluorodeoxycytidine
<220> FEATURE:
<221> NAME/KEY: modified_base
<222> LOCATION: (21)..(21)
<223> OTHER INFORMATION: 5-F-deoxyuridine or 2',2'-difluorodeoxycytidine
<220> FEATURE:
<221> NAME/KEY: modified_base
<222> LOCATION: (24)..(24)
<223> OTHER INFORMATION: 5-F-deoxyuridine or 2',2'-difluorodeoxycytidine
<220> FEATURE:
<221> NAME/KEY: misc_feature
<222> LOCATION: (1)..(26)
<223> OTHER INFORMATION: All "n's" are defined the same (i.e. if "n" is defined as 5-F-deoxyuridine, then all "n's" are defined as 5-F-deoxyuridine)
<220> FEATURE:
<221> NAME/KEY: misc_feature
<222> LOCATION: (1)..(26)
<223> OTHER INFORMATION: If "n's" are defined as "u's", the sequence would be described as an artificial combined molecule

<400> SEQUENCE: 4
ggnggnggng gnngnggngg nggngg                                          26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (3)..(3)
<223> OTHER INFORMATION: 5-F-deoxyuridine
<220> FEATURE:
<221> NAME/KEY: modified_base
<222> LOCATION: (6)..(6)
<223> OTHER INFORMATION: 5-F-deoxyuridine
<220> FEATURE:
<221> NAME/KEY: modified_base
<222> LOCATION: (9)..(9)
<223> OTHER INFORMATION: 5-F-deoxyuridine
<220> FEATURE:
<221> NAME/KEY: modified_base
<222> LOCATION: (12)..(15)
<223> OTHER INFORMATION: 5-F-deoxyuridine
<220> FEATURE:
<221> NAME/KEY: modified_base
<222> LOCATION: (18)..(18)
<223> OTHER INFORMATION: 5-F-deoxyuridine
<220> FEATURE:
<221> NAME/KEY: modified_base
<222> LOCATION: (21)..(21)
<223> OTHER INFORMATION: 5-F-deoxyuridine
<220> FEATURE:
<221> NAME/KEY: modified_base
<222> LOCATION: (24)..(24)
<223> OTHER INFORMATION: 5-F-deoxyuridine

<400> SEQUENCE: 5
ggnggnggng gnnnnggngg nggngg                                          26

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (4)..(7)
<223> OTHER INFORMATION: 5-F-deoxyuridine or 2',2'-difluorodeoxycytidine
<220> FEATURE:
<221> NAME/KEY: modified_base
<222> LOCATION: (11)..(14)
<223> OTHER INFORMATION: 5-F-deoxyuridine or 2',2'-difluorodeoxycytidine
<220> FEATURE:
<221> NAME/KEY: modified_base
<222> LOCATION: (18)..(21)
<223> OTHER INFORMATION: 5-F-deoxyuridine or 2',2'-difluorodeoxycytidine
<220> FEATURE:
<221> NAME/KEY: misc_feature
<222> LOCATION: (1)..(24)

```
<223> OTHER INFORMATION: All "n's" are defined the same (i.e. if "n" is
      defined as 5-F-deoxyuridine, then all "n's" are defined as
      5-F-deoxyuridine)
<220> FEATURE:
<221> NAME/KEY: misc_feature
<222> LOCATION: (1)..(24)
<223> OTHER INFORMATION: If "n's" are defined as "u's", the sequence
      would be described as an artificial combined molecule

<400> SEQUENCE: 6
gggnnnnggg nnnngggnnn nggg                                            24

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-F-deoxyuridine, 2',2'-difluorodeoxycytidine
      or Cytosine arabinoside
<220> FEATURE:
<221> NAME/KEY: modified_base
<222> LOCATION: (6)..(9)
<223> OTHER INFORMATION: 5-F-deoxyuridine, 2',2'-difluorodeoxycytidine
      or Cytosine arabinoside
<220> FEATURE:
<221> NAME/KEY: modified_base
<222> LOCATION: (12)..(12)
<223> OTHER INFORMATION: 5-F-deoxyuridine, 2',2'-difluorodeoxycytidine
      or Cytosine arabinoside
<220> FEATURE:
<221> NAME/KEY: misc_feature
<222> LOCATION: (1)..(14)
<223> OTHER INFORMATION: All "n's" are defined the same (i.e. if "n" is
      defined as 5-F-deoxyuridine, then all "n's" are defined as
      5-F-deoxyuridine)
<220> FEATURE:
<221> NAME/KEY: misc_feature
<222> LOCATION: (1)..(14)
<223> OTHER INFORMATION: If "n's" are defined as "u's", the sequence
      would be described as an artificial combined molecule

<400> SEQUENCE: 7
ggnggnnnng gngg                                                       14

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 5-F-deoxyuridine
<220> FEATURE:
<221> NAME/KEY: modified_base
<222> LOCATION: (6)..(6)
<223> OTHER INFORMATION: 5-F-deoxyuridine
<220> FEATURE:
<221> NAME/KEY: modified_base
<222> LOCATION: (9)..(9)
<223> OTHER INFORMATION: 5-F-deoxyuridine

<400> SEQUENCE: 8
ggnggnggng g                                                          11
```

```
<210> SEQ ID NO 9
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(6)
<223> OTHER INFORMATION: 5-F-deoxyuridine

<400> SEQUENCE: 9 ggnnnngg                                                                    8

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 5-F-deoxyuridine
<220> FEATURE:
<221> NAME/KEY: modified_base
<222> LOCATION: (6)..(6)
<223> OTHER INFORMATION: 5-F-deoxyuridine
<220> FEATURE:
<221> NAME/KEY: modified_base
<222> LOCATION: (9)..(9)
<223> OTHER INFORMATION: 5-F-deoxyuridine
<220> FEATURE:
<221> NAME/KEY: modified_base
<222> LOCATION: (12)..(12)
<223> OTHER INFORMATION: 5-F-deoxyuridine
<220> FEATURE:
<221> NAME/KEY: modified_base
<222> LOCATION: (21)..(21)
<223> OTHER INFORMATION: 5-F-deoxyuridine
<220> FEATURE:
<221> NAME/KEY: modified_base
<222> LOCATION: (24)..(24)
<223> OTHER INFORMATION: 5-F-deoxyuridine
<220> FEATURE:
<221> NAME/KEY: modified_base
<222> LOCATION: (27)..(27)
<223> OTHER INFORMATION: 5-F-deoxyuridine

<400> SEQUENCE: 10
nnnggnggng gnggttgtgg nggnggngg                                             29

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
```

```
<223> OTHER INFORMATION: 5-F-deoxyuridine
<220> FEATURE:
<221> NAME/KEY: modified_base
<222> LOCATION: (15)..(16)
<223> OTHER INFORMATION: 5-F-deoxyuridine
<220> FEATURE:
<221> NAME/KEY: modified_base
<222> LOCATION: (18)..(18)
<223> OTHER INFORMATION: 5-F-deoxyuridine

<400> SEQUENCE: 11
nnnggtggtg gtggnngngg tggtggtgg                                             29

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 5-F-deoxyuridine
<220> FEATURE:
<221> NAME/KEY: modified_base
<222> LOCATION: (6)..(6)
<223> OTHER INFORMATION: 5-F-deoxyuridine
<220> FEATURE:
<221> NAME/KEY: modified_base
<222> LOCATION: (9)..(9)
<223> OTHER INFORMATION: 5-F-deoxyuridine
<220> FEATURE:
<221> NAME/KEY: modified_base
<222> LOCATION: (18)..(18)
<223> OTHER INFORMATION: 5-F-deoxyuridine
<220> FEATURE:
<221> NAME/KEY: modified_base
<222> LOCATION: (21)..(21)
<223> OTHER INFORMATION: 5-F-deoxyuridine
<220> FEATURE:
<221> NAME/KEY: modified_base
<222> LOCATION: (24)..(24)
<223> OTHER INFORMATION: 5-F-deoxyuridine

<400> SEQUENCE: 12
ggnggnggng gttttggngg nggngg                                                26

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-F-deoxyuridine or Cytosine arabinoside
<220> FEATURE:
<221> NAME/KEY: modified_base
<222> LOCATION: (6)..(6)
<223> OTHER INFORMATION: 5-F-deoxyuridine or Cytosine arabinoside
<220> FEATURE:
<221> NAME/KEY: modified_base
<222> LOCATION: (9)..(9)
<223> OTHER INFORMATION: 5-F-deoxyuridine or Cytosine arabinoside
<220> FEATURE:
<221> NAME/KEY: modified_base
<222> LOCATION: (18)..(18)
<223> OTHER INFORMATION: 5-F-deoxyuridine or Cytosine arabinoside
<220> FEATURE:
```

```
<221> NAME/KEY: modified_base
<222> LOCATION: (21)..(21)
<223> OTHER INFORMATION: 5-F-deoxyuridine or Cytosine arabinoside
<220> FEATURE:
<221> NAME/KEY: modified_base
<222> LOCATION: (24)..(24)
<223> OTHER INFORMATION: 5-F-deoxyuridine or Cytosine arabinoside
<220> FEATURE:
<221> NAME/KEY: misc_feature
<222> LOCATION: (1)..(26)
<223> OTHER INFORMATION: All "n's" are defined the same (i.e. if "n" is
      defined as 5-F-deoxyuridine, then all "n's" are defined as
      5-F-deoxyuridine)
<220> FEATURE:
<221> NAME/KEY: misc_feature
<222> LOCATION: (1)..(26)
<223> OTHER INFORMATION: If "n's" are defined as "u's", the sequence
      would be described as an artificial combined molecule

<400> SEQUENCE: 13
ggnggnggng gccccggngg nggngg                                         26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(15)
<223> OTHER INFORMATION: 5-F-deoxyuridine

<400> SEQUENCE: 14
ggtggtggtg gnnnnggtgg tggtgg                                         26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 5-F-deoxyuridine
<220> FEATURE:
<221> NAME/KEY: modified_base
<222> LOCATION: (6)..(6)
<223> OTHER INFORMATION: 5-F-deoxyuridine
<220> FEATURE:
<221> NAME/KEY: modified_base
<222> LOCATION: (9)..(9)
<223> OTHER INFORMATION: 5-F-deoxyuridine
<220> FEATURE:
<221> NAME/KEY: modified_base
<222> LOCATION: (12)..(15)
<223> OTHER INFORMATION: 5-F-deoxyuridine

<400> SEQUENCE: 15
ggnggnggng gnnnnggtgg tggtgg                                         26

<210> SEQ ID NO 16
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(15)
<223> OTHER INFORMATION: 5-F-deoxyuridine
<220> FEATURE:
<221> NAME/KEY: modified_base
<222> LOCATION: (18)..(18)
<223> OTHER INFORMATION: 5-F-deoxyuridine
<220> FEATURE:
<221> NAME/KEY: modified_base
<222> LOCATION: (21)..(21)
<223> OTHER INFORMATION: 5-F-deoxyuridine
<220> FEATURE:
<221> NAME/KEY: modified_base
<222> LOCATION: (24)..(24)
<223> OTHER INFORMATION: 5-F-deoxyuridine

<400> SEQUENCE: 16
ggtggtggtg gnnnnggngg nggngg                                       26

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 5-F-deoxyuridine
<220> FEATURE:
<221> NAME/KEY: modified_base
<222> LOCATION: (6)..(6)
<223> OTHER INFORMATION: 5-F-deoxyuridine
<220> FEATURE:
<221> NAME/KEY: modified_base
<222> LOCATION: (15)..(15)
<223> OTHER INFORMATION: 5-F-deoxyuridine
<220> FEATURE:
<221> NAME/KEY: modified_base
<222> LOCATION: (18)..(18)
<223> OTHER INFORMATION: 5-F-deoxyuridine

<400> SEQUENCE: 17
ggnggnggtt ttggnggngg                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(12)
<223> OTHER INFORMATION: Cytosine arabinoside or 5-F-deoxyuridine
<220> FEATURE:
<221> NAME/KEY: misc_feature
<222> LOCATION: (1)..(20)
<223> OTHER INFORMATION: All "n's" are defined the same (i.e. if "n" is
      defined as Cytosine arabinoside, then all "n's" are defined as
      Cytosine arabinoside
<220> FEATURE:
```

```
<221> NAME/KEY: misc_feature
<222> LOCATION: (1)..(20)
<223> OTHER INFORMATION: If "n's" are defined as "u's", the sequence
      would be described as an artificial combined molecule

<400> SEQUENCE: 18
ggtggtggnn nnggtggtgg                                                    20

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 5-F-deoxyuridine
<220> FEATURE:
<221> NAME/KEY: modified_base
<222> LOCATION: (12)..(12)
<223> OTHER INFORMATION: 5-F-deoxyuridine

<400> SEQUENCE: 19
ggnggttttg gngg                                                          14

<210> SEQ ID NO 20
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(9)
<223> OTHER INFORMATION: 5-F-deoxyuridine

<400> SEQUENCE: 20
ggtggnnnng gtgg                                                          14

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 5-F-deoxyuridine
<220> FEATURE:
<221> NAME/KEY: modified_base
<222> LOCATION: (9)..(9)
<223> OTHER INFORMATION: 5-F-deoxyuridine

<400> SEQUENCE: 21
ggnggtggng g                                                             11

<210> SEQ ID NO 22
```

```
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(5)
<223> OTHER INFORMATION: 5-F-deoxyuridine

<400> SEQUENCE: 22 ggtnntgg                                                                    8

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(11)
<223> OTHER INFORMATION: 5-F-deoxyuridine or 2',2'-difluorodeoxycytidine
<220> FEATURE:
<221> NAME/KEY: misc_feature
<222> LOCATION: (1)..(20)
<223> OTHER INFORMATION: All "n's" are defined the same (i.e. if "n" is
      defined as 5-F-deoxyuridine, then all "n's" are defined as
      5-F-deoxyuridine)
<220> FEATURE:
<221> NAME/KEY: misc_feature
<222> LOCATION: (1)..(20)
<223> OTHER INFORMATION: If "n's" are defined as "u's", the sequence
      would be described as an artificial combined molecule

<400> SEQUENCE: 23
ggtggtggtn ntggtggtgg                                                      20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 5-F-deoxyuridine or 2',2'-difluorodeoxycytidine
<220> FEATURE:
<221> NAME/KEY: misc_feature
<222> LOCATION: (1)..(20)
<223> OTHER INFORMATION: If "n's" are defined as "u's", the sequence
      would be described as an artificial combined molecule

<400> SEQUENCE: 24
ggtggtggtt ntggtggtgg                                                      20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<220> FEATURE:
<221> NAME/KEY: modified_base
<222> LOCATION: (12)..(12)
<223> OTHER INFORMATION: 5-F-deoxyuridine

<400> SEQUENCE: 25
ggtggtggtt tnggtggtgg                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(12)
<223> OTHER INFORMATION: 5-F-deoxyuridine

<400> SEQUENCE: 26
ggtggtggtn nnggtggtgg                                              20

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(13)
<223> OTHER INFORMATION: 5-F-deoxyuridine
<220> FEATURE:
<221> NAME/KEY: modified_base
<222> LOCATION: (15)..(15)
<223> OTHER INFORMATION: 5-F-deoxyuridine

<400> SEQUENCE: 27
ggtggtggtg gnngnggtgg tggtgg                                       26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (13)..(15)
<223> OTHER INFORMATION: 5-F-deoxyuridine

<400> SEQUENCE: 28
ggtggtggtg gtnnnggtgg tggtgg                                       26

<210> SEQ ID NO 29
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (13)..(14)
<223> OTHER INFORMATION: 5-F-deoxyuridine or 2',2'-difluorodeoxycytidine
<220> FEATURE:
<221> NAME/KEY: misc_feature
<222> LOCATION: (1)..(26)
<223> OTHER INFORMATION: All "n's" are defined the same (i.e. if "n" is
      defined as 5-F-deoxyuridine, then all "n's" are defined as
      5-F-deoxyuridine)
<220> FEATURE:
<221> NAME/KEY: misc_feature
<222> LOCATION: (1)..(26)
<223> OTHER INFORMATION: If "n's" are defined as "u's", the sequence
      would be described as an artificial combined molecule

<400> SEQUENCE: 29
ggtggtggtg gtnntggtgg tggtgg                                      26

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 5-F-deoxyuridine or 2',2'-difluorodeoxycytidine
<220> FEATURE:
<221> NAME/KEY: misc_feature
<222> LOCATION: (1)..(26)
<223> OTHER INFORMATION: All "n's" are defined the same (i.e. if "n" is
      defined as 5-F-deoxyuridine, then all "n's" are defined as
      5-F-deoxyuridine)
<220> FEATURE:
<221> NAME/KEY: misc_feature
<222> LOCATION: (1)..(26)
<223> OTHER INFORMATION: If "n's" are defined as "u's", the sequence
      would be described as an artificial combined molecule

<400> SEQUENCE: 30
ggtggtggtg gttntggtgg tggtgg                                      26

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (15)..(15)
<223> OTHER INFORMATION: 5-F-deoxyuridine

<400> SEQUENCE: 31
ggtggtggtg gttgnggtgg tggtgg                                      26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 5-F-deoxyuridine
<220> FEATURE:
<221> NAME/KEY: modified_base
<222> LOCATION: (6)..(6)
<223> OTHER INFORMATION: 5-F-deoxyuridine
<220> FEATURE:
<221> NAME/KEY: modified_base
<222> LOCATION: (9)..(9)
<223> OTHER INFORMATION: 5-F-deoxyuridine
<220> FEATURE:
<221> NAME/KEY: modified_base
<222> LOCATION: (18)..(18)
<223> OTHER INFORMATION: 5-F-deoxyuridine
<220> FEATURE:
<221> NAME/KEY: modified_base
<222> LOCATION: (21)..(21)
<223> OTHER INFORMATION: 5-F-deoxyuridine
<220> FEATURE:
<221> NAME/KEY: modified_base
<222> LOCATION: (24)..(24)
<223> OTHER INFORMATION: 5-F-deoxyuridine

<400> SEQUENCE: 32
ggnggnggng gttgtggngg nggngg                                          26

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 5-F-deoxyuridine
<220> FEATURE:
<221> NAME/KEY: modified_base
<222> LOCATION: (6)..(6)
<223> OTHER INFORMATION: 5-F-deoxyuridine
<220> FEATURE:
<221> NAME/KEY: modified_base
<222> LOCATION: (21)..(21)
<223> OTHER INFORMATION: 5-F-deoxyuridine
<220> FEATURE:
<221> NAME/KEY: modified_base
<222> LOCATION: (24)..(24)
<223> OTHER INFORMATION: 5-F-deoxyuridine

<400> SEQUENCE: 33
ggnggnggtg gttgtggtgg nggngg                                          26

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-F-deoxycytidine
<220> FEATURE:
<221> NAME/KEY: modified_base
<222> LOCATION: (24)..(24)
<223> OTHER INFORMATION: 5-F-deoxycytidine
```

```
<400> SEQUENCE: 34
ggnggtggtg gttgtggtgg tggngg                                       26

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2',2'-difluorodeoxycytidine

<400> SEQUENCE: 35
nnggtggtgg tggttgtggt ggtggtgg                                     28

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2',2'-difluorodeoxycytidine

<400> SEQUENCE: 36
nggtggtggt ggttgtggtg gtggtgg                                      27

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: 2',2'-difluorodeoxycytidine

<400> SEQUENCE: 37
ggtggtggnt gtggtggtgg                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 2',2'-difluorodeoxycytidine

<400> SEQUENCE: 38
ggtggtggtn gtggtggtgg                                              20

<210> SEQ ID NO 39
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: 2',2'-difluorodeoxycytidine

<400> SEQUENCE: 39
ggtggtggtt gnggtggtgg                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 2',2'-difluorodeoxycytidine
<220> FEATURE:
<221> NAME/KEY: modified_base
<222> LOCATION: (12)..(12)
<223> OTHER INFORMATION: 2',2'-difluorodeoxycytidine

<400> SEQUENCE: 40
ggtggtggtn gnggtggtgg                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2',2'-difluorodeoxycytidine
<220> FEATURE:
<221> NAME/KEY: modified_base
<222> LOCATION: (18)..(18)
<223> OTHER INFORMATION: 2',2'-difluorodeoxycytidine

<400> SEQUENCE: 41
ggnggtggtt gtggtggngg                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2',2'-difluorodeoxycytidine
<220> FEATURE:
<221> NAME/KEY: modified_base
<222> LOCATION: (15)..(15)
<223> OTHER INFORMATION: 2',2'-difluorodeoxycytidine

<400> SEQUENCE: 42
ggtggnggtt gtggnggtgg                                              20

<210> SEQ ID NO 43
<211> LENGTH: 26
<212> TYPE: DNA
<213> ORGANISM: Artificial Sequence
```

<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 2',2'-difluorodeoxycytidine

<400> SEQUENCE: 43
ggtggtggtg gtngtggtgg tggtgg                                        26

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 2',2'-difluorodeoxycytidine
<220> FEATURE:
<221> NAME/KEY: modified_base
<222> LOCATION: (15)..(15)
<223> OTHER INFORMATION: 2',2'-difluorodeoxycytidine

<400> SEQUENCE: 44
ggtggtggtg gtngnggtgg tggtgg                                        26

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2',2'-difluorodeoxycytidine

<400> SEQUENCE: 45
ggnggtggtg gttgtggtgg tggtgg                                        26

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2',2'-difluorodeoxycytidine
<220> FEATURE:
<221> NAME/KEY: modified_base
<222> LOCATION: (21)..(21)
<223> OTHER INFORMATION: 2',2'-difluorodeoxycytidine

<400> SEQUENCE: 46
ggtggnggtg gttgtggtgg nggtgg                                        26

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (11)..(11)
<223> OTHER INFORMATION: 2',2'-difluorodeoxycytidine
<220> FEATURE:
<221> NAME/KEY: modified_base
<222> LOCATION: (21)..(21)
<223> OTHER INFORMATION: 2',2'-difluorodeoxycytidine

<400> SEQUENCE: 47
ggtggtggtt ntggtggtgg n                                              21

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tttggtggtg gtggttgtgg tggtggtgg                                      29

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tttcctcctc ctccttctcc tcctcctcc                                      29

<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tttggtggtg gtggttgtgg tggtggtgg                                      29

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggtggtggtg gttgtggtgg tggtgg                                         26

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
```

```
<223> OTHER INFORMATION: 5-fluorodeoxyuridine
<220> FEATURE:
<221> NAME/KEY: modified_base
<222> LOCATION: (6)..(6)
<223> OTHER INFORMATION: 5-fluorodeoxyuridine
<220> FEATURE:
<221> NAME/KEY: modified_base
<222> LOCATION: (9)..(9)
<223> OTHER INFORMATION: 5-fluorodeoxyuridine
<220> FEATURE:
<221> NAME/KEY: modified_base
<222> LOCATION: (12)..(12)
<223> OTHER INFORMATION: 5-fluorodeoxyuridine
<220> FEATURE:
<221> NAME/KEY: modified_base
<222> LOCATION: (15)..(16)
<223> OTHER INFORMATION: 5-fluorodeoxyuridine
<220> FEATURE:
<221> NAME/KEY: modified_base
<222> LOCATION: (18)..(18)
<223> OTHER INFORMATION: 5-fluorodeoxyuridine
<220> FEATURE:
<221> NAME/KEY: modified_base
<222> LOCATION: (21)..(21)
<223> OTHER INFORMATION: 5-fluorodeoxyuridine
<220> FEATURE:
<221> NAME/KEY: modified_base
<222> LOCATION: (24)..(24)
<223> OTHER INFORMATION: 5-fluorodeoxyuridine
<220> FEATURE:
<221> NAME/KEY: modified_base
<222> LOCATION: (27)..(27)
<223> OTHER INFORMATION: 5-fluorodeoxyuridine

<400> SEQUENCE: 52
nnnggnggng gnggnngngg nggnggngg                                           29

<210> SEQ ID NO 53
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 5-fluorodeoxyuridine

<400> SEQUENCE: 53
nnnggtggtg gtggttgtgg tggtggtgg                                           29

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 5-fluorodeoxyuridine
<220> FEATURE:
<221> NAME/KEY: modified_base
<222> LOCATION: (6)..(6)
<223> OTHER INFORMATION: 5-fluorodeoxyuridine
<220> FEATURE:
<221> NAME/KEY: modified_base
```

```
<222> LOCATION: (9)..(9)
<223> OTHER INFORMATION: 5-fluorodeoxyuridine
<220> FEATURE:
<221> NAME/KEY: modified_base
<222> LOCATION: (12)..(13)
<223> OTHER INFORMATION: 5-fluorodeoxyuridine
<220> FEATURE:
<221> NAME/KEY: modified_base
<222> LOCATION: (15)..(15)
<223> OTHER INFORMATION: 5-fluorodeoxyuridine
<220> FEATURE:
<221> NAME/KEY: modified_base
<222> LOCATION: (18)..(18)
<223> OTHER INFORMATION: 5-fluorodeoxyuridine
<220> FEATURE:
<221> NAME/KEY: modified_base
<222> LOCATION: (21)..(21)
<223> OTHER INFORMATION: 5-fluorodeoxyuridine
<220> FEATURE:
<221> NAME/KEY: modified_base
<222> LOCATION: (24)..(24)
<223> OTHER INFORMATION: 5-fluorodeoxyuridine

<400> SEQUENCE: 54
ggnggnggng gnngnggngg nggngg                                26

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 5-fluorodeoxyuridine
<220> FEATURE:
<221> NAME/KEY: modified_base
<222> LOCATION: (6)..(6)
<223> OTHER INFORMATION: 5-fluorodeoxyuridine
<220> FEATURE:
<221> NAME/KEY: modified_base
<222> LOCATION: (9)..(9)
<223> OTHER INFORMATION: 5-fluorodeoxyuridine
<220> FEATURE:
<221> NAME/KEY: modified_base
<222> LOCATION: (12)..(15)
<223> OTHER INFORMATION: 5-fluorodeoxyuridine
<220> FEATURE:
<221> NAME/KEY: modified_base
<222> LOCATION: (18)..(18)
<223> OTHER INFORMATION: 5-fluorodeoxyuridine
<220> FEATURE:
<221> NAME/KEY: modified_base
<222> LOCATION: (21)..(21)
<223> OTHER INFORMATION: 5-fluorodeoxyuridine
<220> FEATURE:
<221> NAME/KEY: modified_base
<222> LOCATION: (24)..(24)
<223> OTHER INFORMATION: 5-fluorodeoxyuridine

<400> SEQUENCE: 55
ggnggnggng gnnnnggngg nggngg                                26

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 5-fluorodeoxyuridine
<220> FEATURE:
<221> NAME/KEY: modified_base
<222> LOCATION: (6)..(6)
<223> OTHER INFORMATION: 5-fluorodeoxyuridine
<220> FEATURE:
<221> NAME/KEY: modified_base
<222> LOCATION: (9)..(9)
<223> OTHER INFORMATION: 5-fluorodeoxyuridine
<220> FEATURE:
<221> NAME/KEY: modified_base
<222> LOCATION: (18)..(18)
<223> OTHER INFORMATION: 5-fluorodeoxyuridine
<220> FEATURE:
<221> NAME/KEY: modified_base
<222> LOCATION: (21)..(21)
<223> OTHER INFORMATION: 5-fluorodeoxyuridine
<220> FEATURE:
<221> NAME/KEY: modified_base
<222> LOCATION: (24)..(24)
<223> OTHER INFORMATION: 5-fluorodeoxyuridine

<400> SEQUENCE: 56
ggnggnggng gttgtggngg nggngg                                              26

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 5-fluorodeoxyuridine
<220> FEATURE:
<221> NAME/KEY: modified_base
<222> LOCATION: (6)..(6)
<223> OTHER INFORMATION: 5-fluorodeoxyuridine
<220> FEATURE:
<221> NAME/KEY: modified_base
<222> LOCATION: (21)..(21)
<223> OTHER INFORMATION: 5-fluorodeoxyuridine
<220> FEATURE:
<221> NAME/KEY: modified_base
<222> LOCATION: (24)..(24)
<223> OTHER INFORMATION: 5-fluorodeoxyuridine

<400> SEQUENCE: 57
ggnggnggtg gttgtggtgg nggngg                                              26

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 5-fluorodeoxyuridine
```

```
<220> FEATURE:
<221> NAME/KEY: modified_base
<222> LOCATION: (24)..(24)
<223> OTHER INFORMATION: 5-fluorodeoxyuridine

<400> SEQUENCE: 58
ggnggtggtg gttgtggtgg tggng                                              25

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(15)
<223> OTHER INFORMATION: 5-fluorodeoxyuridine

<400> SEQUENCE: 59
ggtggtggtg gnnnnggtgg tggtgg                                             26

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(13)
<223> OTHER INFORMATION: 5-fluorodeoxyuridine
<220> FEATURE:
<221> NAME/KEY: modified_base
<222> LOCATION: (15)..(15)
<223> OTHER INFORMATION: 5-fluorodeoxyuridine

<400> SEQUENCE: 60
ggtggtggtg gnngnggtgg tggtgg                                             26

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2',2'-difluorodeoycytidine/gemcitabine
<220> FEATURE:
<221> NAME/KEY: modified_base
<222> LOCATION: (6)..(6)
<223> OTHER INFORMATION: 2',2'-difluorodeoycytidine/gemcitabine
<220> FEATURE:
<221> NAME/KEY: modified_base
<222> LOCATION: (9)..(9)
<223> OTHER INFORMATION: 2',2'-difluorodeoycytidine/gemcitabine
<220> FEATURE:
<221> NAME/KEY: modified_base
<222> LOCATION: (12)..(13)
<223> OTHER INFORMATION: 2',2'-difluorodeoycytidine/gemcitabine
<220> FEATURE:
<221> NAME/KEY: modified_base
```

```
<222> LOCATION: (15)..(15)
<223> OTHER INFORMATION: 2',2'-difluorodeoycytidine/gemcitabine
<220> FEATURE:
<221> NAME/KEY: modified_base
<222> LOCATION: (18)..(18)
<223> OTHER INFORMATION: 2',2'-difluorodeoycytidine/gemcitabine
<220> FEATURE:
<221> NAME/KEY: modified_base
<222> LOCATION: (21)..(21)
<223> OTHER INFORMATION: 2',2'-difluorodeoycytidine/gemcitabine
<220> FEATURE:
<221> NAME/KEY: modified_base
<222> LOCATION: (24)..(24)
<223> OTHER INFORMATION: 2',2'-difluorodeoycytidine/gemcitabine

<400> SEQUENCE: 61
ggnggnggng gnngnggngg nggngg                                              26

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 2',2'-difluorodeoycytidine/gemcitabine

<400> SEQUENCE: 62
ggtggtggtg gttntggtgg tggtgg                                              26

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(14)
<223> OTHER INFORMATION: 2',2'-difluorodeoycytidine/gemcitabine

<400> SEQUENCE: 63
ggtggtggtg gtnntggtgg tggtgg                                              26

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 2',2'-difluorodeoycytidine/gemcitabine

<400> SEQUENCE: 64
ggtggtggtg gtngtggtgg tggtgg                                              26

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (15)..(15)
<223> OTHER INFORMATION: 2',2'-difluorodeoycytidine/gemcitabine

<400> SEQUENCE: 65
ggtggtggtg gttgnggtgg tggtgg                                              26

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 2',2'-difluorodeoycytidine/gemcitabine
<220> FEATURE:
<221> NAME/KEY: modified_base
<222> LOCATION: (15)..(15)
<223> OTHER INFORMATION: 2',2'-difluorodeoycytidine/gemcitabine

<400> SEQUENCE: 66
ggtggtggtg gtngnggtgg tggtgg                                              26

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2',2'-difluorodeoycytidine/gemcitabine
<220> FEATURE:
<221> NAME/KEY: modified_base
<222> LOCATION: (24)..(24)
<223> OTHER INFORMATION: 2',2'-difluorodeoycytidine/gemcitabine

<400> SEQUENCE: 67
ggnggtggtg gttgtggtgg tggngg                                              26

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2',2'-difluorodeoycytidine/gemcitabine
<220> FEATURE:
<221> NAME/KEY: modified_base
<222> LOCATION: (21)..(21)
<223> OTHER INFORMATION: 2',2'-difluorodeoycytidine/gemcitabine

<400> SEQUENCE: 68
ggtggnggtg gttgtggtgg nggtgg                                              26
```